(12) United States Patent
Farhat et al.

(10) Patent No.: US 9,463,105 B2
(45) Date of Patent: Oct. 11, 2016

(54) METHODS AND APPARATUS FOR LUMINAL STENTING

(71) Applicant: Covidien LP, Mansfield, MA (US)

(72) Inventors: Lawrence Farhat, Carlsbad, CA (US); Edwin Wang, Tustin, CA (US); David Franco, Costa Mesa, CA (US)

(73) Assignee: Covidien LP, Mansfield, MA (US)

( * ) Notice: Subject to any disclaimer, the term of this patent is extended or adjusted under 35 U.S.C. 154(b) by 271 days.

(21) Appl. No.: 13/826,298

(22) Filed: Mar. 14, 2013

(65) Prior Publication Data

US 2014/0277361 A1 Sep. 18, 2014

(51) Int. Cl.
*A61F 2/06* (2013.01)
*A61F 2/966* (2013.01)
*A61M 25/10* (2013.01)
*A61F 2/958* (2013.01)
*A61F 2/95* (2013.01)

(52) U.S. Cl.
CPC ................ *A61F 2/966* (2013.01); *A61F 2/958* (2013.01); *A61F 2002/9528* (2013.01); *A61F 2002/9534* (2013.01); *A61F 2002/9583* (2013.01); *A61F 2002/9665* (2013.01); *A61M 25/10* (2013.01); *A61M 2025/1093* (2013.01)

(58) Field of Classification Search
CPC .................... A61M 25/10; A61M 2025/1081; A61M 2025/1093; A61F 2/958; A61F 2/966; A61F 2002/9583
See application file for complete search history.

(56) References Cited

U.S. PATENT DOCUMENTS

| | | |
|---|---|---|
| 3,108,593 A | 10/1963 | Glassman |
| 4,425,908 A | 1/1984 | Simon |
| 4,619,246 A | 10/1986 | Molgaard-Nielsen et al. |
| 4,655,771 A | 4/1987 | Wallsten |
| 4,768,507 A | 9/1988 | Fischell et al. |
| 4,921,484 A | 5/1990 | Hillstead |
| 4,998,539 A | 3/1991 | Delsanti |
| 5,026,377 A | 6/1991 | Burton et al. |
| 5,061,275 A | 10/1991 | Wallsten et al. |
| 5,064,435 A | 11/1991 | Porter |

(Continued)

FOREIGN PATENT DOCUMENTS

| | | |
|---|---|---|
| CA | 2607529 | 4/2008 |
| CA | 2607529 A1 | 4/2008 |

(Continued)

OTHER PUBLICATIONS

U.S. Appl. No. 13/669,652, filed Nov. 6, 2012.

(Continued)

*Primary Examiner* — Robert Lynch
(74) *Attorney, Agent, or Firm* — Mark J. Kertz, Esq.

(57) ABSTRACT

Stent delivery systems and methods of use are provided. The systems can include a catheter, a core member, and engagement member, and a stent. The catheter can have a inner wall. The core member can extend within the catheter and having a distal segment. The engagement member can be attached to the distal segment. Further, the stent can be positioned within the catheter and extend over the engagement member. The stent can have an axial length that is greater than an axial length of the engagement member. The engagement member can have an expanded state in which the engagement member presses the stent against the catheter inner wall for engaging the stent to move the stent along with the core member relative to the catheter.

14 Claims, 14 Drawing Sheets

(56) References Cited

U.S. PATENT DOCUMENTS

| | | |
|---|---|---|
| 5,104,404 A | 4/1992 | Wolff |
| 5,122,136 A | 6/1992 | Guglielmi et al. |
| 5,158,548 A | 10/1992 | Lau et al. |
| 5,222,971 A | 6/1993 | Willard et al. |
| 5,250,071 A | 10/1993 | Palermo |
| 5,334,210 A | 8/1994 | Gianturco |
| 5,378,239 A | 1/1995 | Termin et al. |
| 5,405,379 A | 4/1995 | Lane |
| 5,425,984 A | 6/1995 | Kennedy et al. |
| 5,484,444 A | 1/1996 | Braunschweiler et al. |
| 5,499,981 A | 3/1996 | Kordis |
| 5,527,338 A | 6/1996 | Purdy |
| 5,545,208 A | 8/1996 | Wolff et al. |
| 5,545,209 A | 8/1996 | Roberts et al. |
| 5,549,635 A | 8/1996 | Solar |
| 5,624,461 A | 4/1997 | Mariant |
| 5,634,942 A | 6/1997 | Chevillon et al. |
| 5,645,558 A | 7/1997 | Horton |
| 5,662,703 A | 9/1997 | Yurek et al. |
| 5,690,671 A | 11/1997 | McGurk et al. |
| 5,702,419 A | 12/1997 | Berry et al. |
| 5,713,907 A | 2/1998 | Hogendijk et al. |
| 5,725,552 A | 3/1998 | Kotula et al. |
| 5,728,906 A | 3/1998 | Eguchi et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,749,920 A | 5/1998 | Quiachon et al. |
| 5,766,151 A | 6/1998 | Valley et al. |
| 5,814,062 A | 9/1998 | Sepetka et al. |
| 5,830,230 A | 11/1998 | Berryman et al. |
| 5,846,261 A | 12/1998 | Kotula et al. |
| 5,853,422 A | 12/1998 | Huebsch et al. |
| 5,855,578 A | 1/1999 | Guglielmi et al. |
| 5,879,366 A | 3/1999 | Shaw et al. |
| 5,908,435 A | 6/1999 | Samuels |
| 5,911,731 A | 6/1999 | Pham et al. |
| 5,916,235 A | 6/1999 | Guglielmi |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,738 A | 8/1999 | Amplatz et al. |
| 5,951,599 A | 9/1999 | McCrory |
| 5,957,948 A | 9/1999 | Mariant |
| 5,976,162 A | 11/1999 | Doan et al. |
| 5,980,554 A | 11/1999 | Lenker et al. |
| 6,001,092 A | 12/1999 | Mirigian et al. |
| 6,010,517 A | 1/2000 | Baccaro |
| 6,024,756 A | 2/2000 | Huebsch et al. |
| 6,033,423 A | 3/2000 | Ken et al. |
| 6,036,720 A | 3/2000 | Abrams et al. |
| 6,059,813 A | 5/2000 | Vrba et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,096,034 A | 8/2000 | Kupiecki et al. |
| 6,096,073 A | 8/2000 | Webster et al. |
| 6,099,526 A | 8/2000 | Whayne et al. |
| 6,106,530 A | 8/2000 | Harada |
| 6,110,191 A | 8/2000 | Dehdashtian et al. |
| 6,123,715 A | 9/2000 | Amplatz |
| 6,139,564 A | 10/2000 | Teoh |
| 6,152,144 A | 11/2000 | Lesh et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,495 B1 | 2/2001 | Lenker et al. |
| 6,190,402 B1 | 2/2001 | Horton et al. |
| 6,193,708 B1 | 2/2001 | Ken et al. |
| 6,221,086 B1 | 4/2001 | Forber |
| 6,261,305 B1 | 7/2001 | Marotta et al. |
| 6,280,412 B1 | 8/2001 | Pederson, Jr. et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,361,558 B1 | 3/2002 | Hieshima et al. |
| 6,368,339 B1 | 4/2002 | Amplatz |
| 6,375,668 B1 | 4/2002 | Gifford et al. |
| 6,379,372 B1 | 4/2002 | Dehdashtian et al. |
| 6,383,174 B1 | 5/2002 | Eder |
| 6,391,037 B1 | 5/2002 | Greenhalgh |
| 6,409,750 B1 | 6/2002 | Hyodoh et al. |
| 6,428,558 B1 | 8/2002 | Jones et al. |
| 6,443,972 B1 | 9/2002 | Bosma et al. |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,530,934 B1 | 3/2003 | Jacobsen et al. |
| 6,544,278 B1 | 4/2003 | Vrba et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,579,302 B2 | 6/2003 | Duerig et al. |
| 6,579,303 B2 | 6/2003 | Amplatz |
| 6,585,748 B1 | 7/2003 | Jeffree |
| 6,585,756 B1 | 7/2003 | Strecker |
| 6,589,256 B2 | 7/2003 | Forber |
| 6,589,265 B1 | 7/2003 | Palmer et al. |
| 6,592,605 B2 | 7/2003 | Lenker et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,551 B1 | 8/2003 | Sullivan et al. |
| 6,613,074 B1 | 9/2003 | Mitelberg et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,652,555 B1 | 11/2003 | VanTassel et al. |
| 6,652,556 B1 | 11/2003 | VanTassel et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,682,505 B2 | 1/2004 | Bates et al. |
| 6,682,546 B2 | 1/2004 | Amplatz |
| 6,689,150 B1 | 2/2004 | VanTassel et al. |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,709,465 B2 | 3/2004 | Mitchell et al. |
| 6,712,835 B2 | 3/2004 | Mazzocchi et al. |
| 6,723,112 B2 | 4/2004 | Ho et al. |
| 6,723,116 B2 | 4/2004 | Taheri |
| 6,730,108 B2 | 5/2004 | Van Tassel et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-Gawwad |
| RE38,711 E | 3/2005 | Igaki et al. |
| 6,860,893 B2 | 3/2005 | Wallace et al. |

(56) References Cited

U.S. PATENT DOCUMENTS

| | | |
|---|---|---|
| 6,936,055 B1 | 8/2005 | Ken et al. |
| 6,949,103 B2 | 9/2005 | Mazzocchi et al. |
| 6,949,113 B2 | 9/2005 | Van Tassel et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | van der Burg et al. |
| 6,994,717 B2 | 2/2006 | Konya et al. |
| 7,011,671 B2 | 3/2006 | Welch |
| 7,018,401 B1 | 3/2006 | Hyodoh et al. |
| 7,029,487 B2 | 4/2006 | Greene, Jr. et al. |
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | van der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,575,590 B2 | 8/2009 | Watson |
| 7,597,704 B2 | 10/2009 | Frazier et al. |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 8,454,681 B2 | 6/2013 | Holman et al. |
| 9,179,918 B2 | 11/2015 | Levy et al. |
| 2001/0000797 A1 | 5/2001 | Mazzocchi |
| 2001/0007082 A1 | 7/2001 | Dusbabek et al. |
| 2001/0012949 A1 | 8/2001 | Forber |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0111647 A1 | 8/2002 | Khairkhahan et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0143239 A1 | 7/2004 | Zhou et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215229 A1* | 10/2004 | Coyle .................. 606/200 |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0222605 A1 | 10/2005 | Greenhalgh et al. |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |
| 2006/0217799 A1 | 9/2006 | Mailander et al. |

(56) References Cited

U.S. PATENT DOCUMENTS

| | | |
|---|---|---|
| 2006/0229700 A1* | 10/2006 | Acosta .................. A61F 2/915 623/1.11 |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1* | 12/2007 | Olsen ..................... A61F 2/95 623/1.12 |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von Oepen et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1* | 5/2009 | Rust ..................... A61F 2/95 623/1.12 |
| 2009/0143849 A1 | 6/2009 | Ozawa et al. |
| 2009/0143851 A1 | 6/2009 | Paul, Jr. |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2009/0318948 A1 | 12/2009 | Linder et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030200 A1 | 2/2010 | Strauss et al. |
| 2010/0030220 A1 | 2/2010 | Truckai et al. |
| 2010/0036390 A1 | 2/2010 | Gumm |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0222802 A1* | 9/2010 | Gillespie et al. ............. 606/192 |
| 2010/0256667 A1* | 10/2010 | Ashby .................. A61F 5/0036 606/191 |
| 2010/0268260 A1 | 10/2010 | Riina et al. |
| 2010/0274276 A1 | 10/2010 | Chow et al. |
| 2010/0312270 A1 | 12/2010 | McGuckin, Jr. et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |

(56) References Cited

U.S. PATENT DOCUMENTS

| | | |
|---|---|---|
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |
| 2015/0157331 A1 | 6/2015 | Levy et al. |
| 2015/0245932 A1 | 9/2015 | Molaei et al. |

FOREIGN PATENT DOCUMENTS

| | | |
|---|---|---|
| CN | 101472537 A | 7/2009 |
| DE | 1283434 B | 11/1968 |
| DE | 102008028308 A1 | 4/2009 |
| DE | 102010050569 A1 | 5/2012 |
| DE | 102011011510 A1 | 8/2012 |
| EP | 743047 A2 | 11/1996 |
| EP | 775470 | 5/1997 |
| EP | 855170 A2 | 7/1998 |
| EP | 1621148 A1 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2279023 A2 | 2/2011 |
| EP | 2363075 A1 | 9/2011 |
| EP | 2496299 A2 | 9/2012 |
| EP | 2675402 A2 | 12/2013 |
| FR | 2556210 B1 | 4/1988 |
| FR | 2890306 A1 | 3/2007 |
| JP | 11-506686 | 6/1999 |
| JP | 2003520103 A | 7/2003 |
| JP | 2003-524434 A | 8/2003 |
| JP | 2004-049585 A | 2/2004 |
| JP | 2005-522266 A | 7/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-96/01591 A1 | 1/1996 |
| WO | WO-97/26939 A1 | 7/1997 |
| WO | WO-99/03404 A1 | 1/1999 |
| WO | WO-99/05977 A1 | 2/1999 |
| WO | WO-99/08607 A1 | 2/1999 |
| WO | WO-99/08743 A1 | 2/1999 |
| WO | WO-99/40873 A1 | 8/1999 |
| WO | WO-99/62432 A1 | 12/1999 |
| WO | WO-00/57815 A1 | 10/2000 |
| WO | WO-01/93782 A1 | 12/2001 |
| WO | WO-02/00139 A1 | 1/2002 |
| WO | WO-02/071977 A2 | 9/2002 |
| WO | WO-03/037191 A1 | 5/2003 |
| WO | WO-2005/117718 | 12/2005 |
| WO | WO-2006/026744 | 3/2006 |
| WO | WO-2006/034166 A2 | 3/2006 |
| WO | WO-2006/052322 A2 | 5/2006 |
| WO | WO-2006/091891 A2 | 8/2006 |
| WO | WO-2006/119422 A2 | 11/2006 |
| WO | WO 2007/047851 A2 | 4/2007 |
| WO | WO-2007/076480 A2 | 7/2007 |
| WO | WO-2007/095031 A2 | 8/2007 |
| WO | WO-2007/121405 | 10/2007 |
| WO | WO-2008/022327 A2 | 2/2008 |
| WO | WO-2008/109228 A2 | 9/2008 |
| WO | WO-2008/151204 A1 | 12/2008 |
| WO | WO-2008/157507 A2 | 12/2008 |
| WO | WO-2009/076515 A1 | 6/2009 |
| WO | WO-2009/132045 A2 | 10/2009 |
| WO | WO-2009/134337 A1 | 11/2009 |
| WO | WO-2009/135166 A2 | 11/2009 |
| WO | WO-2010/028314 A1 | 3/2010 |
| WO | WO-2010/030991 A1 | 3/2010 |
| WO | WO-2010/147808 A1 | 12/2010 |
| WO | WO-2011/057002 A2 | 5/2011 |
| WO | WO-2011/057277 A2 | 5/2011 |
| WO | WO-2011/130081 | 10/2011 |
| WO | WO-2011/153304 A1 | 12/2011 |
| WO | WO-2012/068175 A2 | 5/2012 |
| WO | WO-2012/112749 A2 | 8/2012 |
| WO | WO-2012/166804 A1 | 12/2012 |

OTHER PUBLICATIONS

U.S. Appl. No. 13/795,556, filed Mar. 12, 2013.
U.S. Appl. No. 13/962,267, filed Aug. 8, 2013.
Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.
Hill et al., "Initial Results of the AMPLATZER Vascular Plug in the Treatment of Congenital Heart Disease, Business Briefing," US Cardiology 2004.
Ronnen, "AMPLATZER Vascular Plug Case Study, Closure of Arteriovenous Fistula Between Deep Femoral Artery and Superficial Femoral Vein," AGA Medical Corporation, May 2007.
U.S. Appl. No. 13/629,678, filed Sep. 28, 2012.

* cited by examiner

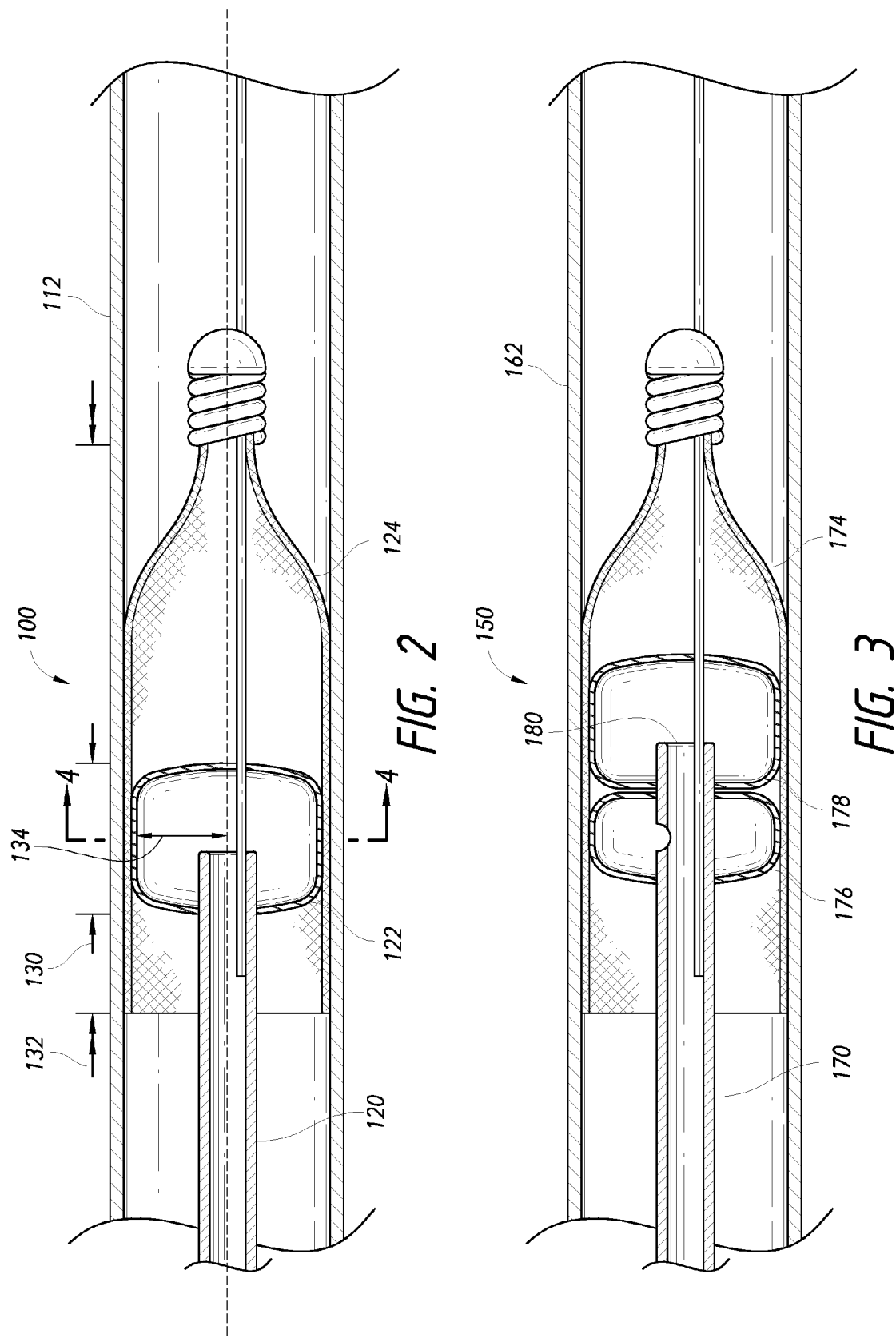

METHODS AND APPARATUS FOR LUMINAL STENTING

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

SUMMARY

At least one aspect of the disclosure provides methods and systems for delivering an occluding device or devices (e.g., stent or stents) in the body. The occluding device can easily conform to the shape of the tortuous vessels of the vasculature. The occluding device can be used in a variety of applications. For example, in some embodiments, the occluding device can direct the blood flow within a vessel away from an aneurysm. Additionally, such an occluding device can allow adequate blood flow to be provided to adjacent structures such that those structures, whether they are branch vessels or oxygen-dependant tissues, are not deprived of the necessary blood flow.

In general, a stent delivery system uses a complex design that gives a clinician maximum control over the delivery and placement of a stent. Such complex systems can be difficult to manufacture and can introduce opportunities for structural failure, material degradation, or inefficiency of cost and time during manufacture and use of the system. Further, it may be very difficult for a clinician to resheath, reposition or withdraw a stent into a catheter of the system after initial exposure of the stent within the vessel, using traditional methods and systems. Furthermore, traditional methods and systems to not provide simple and effective means for ensuring complete apposition of the stent against the vessel wall against which the stent should be positioned.

In accordance with an aspect of at least some embodiments disclosed herein is the realization that a medical device delivery system can have a simple design while allowing a clinician the precision and control necessary for proper stent placement. Further, some embodiments can provide a simple design that reduces the likelihood for error, material degradation, and reduce manufacturing costs.

Additionally, some embodiments can also advantageously enable a clinician to recapture, collapse, withdraw, or resheath a stent within a catheter of the delivery system after the stent has been at least partially exposed or moved distally beyond a distal end of the catheter in order to allow the clinician to improve the placement of the stent within the vessel.

Furthermore, some embodiments can be configured such that the delivery or engagement mechanism for moving the stent within the catheter can also be used for ensuring that the stent is expanded into apposition with the vessel wall after placement within the vessel.

Moreover, some embodiments can be provided such that the delivery system can engage and retain a stent without requiring special-purpose engagement structures on the stent. For example, in accordance with some embodiments, a delivery system can be configured with a highly compliant engagement or constraining mechanism can be used in the delivery of the stent to the target site. The engagement mechanism can provide an engagement between the stent and a core member of the delivery system. The engagement mechanism can comprise an expandable engagement member that can be selectively placed into contact with the stent to urge or carry the stent through a catheter of the delivery system. Additionally, the engagement mechanism can allow the clinician to adjust the settings or configuration of engagement with the stent in response to situational or geometric challenges during advancement of the stent and/or during expansion of the stent.

For example, the engagement mechanism can comprise a selectively expandable member that can be actuated by the clinician to engage, disengage, and/or modify the engagement between the engagement mechanism, the stent, and/or other components of the delivery system. The engagement mechanism can cooperate with another component, such as the catheter inner wall, to form a gripping mechanism that can grip, secure, or restrict the axial movement of the stent relative to the core member.

According to some embodiments, the gripping mechanism can engage a portion of the stent within the catheter lumen. The gripping mechanism can provide a press fit between the engagement mechanism and the catheter inner wall to enable the stent to be advanced, withdrawn, recaptured, retracted, or resheathed into the catheter even after the stent has been moved partially out of the catheter lumen and the stent has at least partially expanded into apposition with the vessel wall. Thus, the gripping mechanism can exert a distal pushing force on the stent to distally advance the stent relative to the catheter until the proximal portion of the stent is distally beyond a distal end of the catheter. Further, the gripping mechanism can also exert a proximal pulling force on the stent, for example, to proximally withdraw the stent into the catheter when a portion of the stent is positioned distally beyond the distal end of the catheter and the stent is at least partially expanded into apposition with a vessel wall. The gripping mechanism can be configured to exert the distal pushing force and the proximal pulling force on its own without the cooperation of other components or structures, such as an intervening structure or mechanism.

The gripping mechanism of some embodiments can therefore exert a generally radially oriented pressing force to capture the stent between the engagement member and the inner wall of the catheter lumen. The engagement member can therefore transmit an axial force from the core assembly to the stent, thereby resulting in distal or proximal axial movement of the stent within the catheter lumen.

Additionally, the engagement member can also be used to make sure that the stent is fully expanded into apposition with the blood vessel by being expanded within the stent lumen and "painting open" or "brushing" against the interior surface of the stent. For example, the engagement member can be expandable to a diameter greater than a diameter of the catheter lumen.

Thus, the engagement member can be used to accomplish various functions of the system. This useful design can tend to be simpler and less complex than various prior art devices, which can increase the clinician's confidence in delivering the stent, reduce manufacturing time, reduce probability of error or a function, reduce the cost, and reduce the time required to perform the procedure.

In some embodiments, the engagement mechanism can comprise at least one balloon that is attached to a distal segment of a core member. The balloon can be inflated within a lumen of the stent to cause the stent to be pressed against a lubricious catheter inner wall of the system. The balloon can frictionally engage the interior of the stent (which frictional force is much greater than the frictional force between the stent and the catheter inner wall) and help move the stent when the balloon and core wire are moved within the catheter lumen. Thus, some embodiments can obviate the need for a proximal bumper that would otherwise be used to contact a proximal end of the stent in order to transmit a distal pushing force to the stent.

The engagement mechanism can comprise a plurality of balloons or engagement members that are arranged in diverse circumferential or axial patterns. Each of the plurality of balloons can have a different axial length, axial spacing relative to other balloons or structures, a different axial location along the core member, etc. The plurality of balloons or engagement members can also be independently or collectively actuatable, which can allow a clinician to more precisely control the engagement between the core assembly and the stent as the core assembly advances through the catheter lumen. This feature can be particularly useful in tortuous vessel anatomies, where a clinician may need to reduce the size or pressure of a balloon or engagement member in order to protect the stent or reduce the required pushing force to advance the core assembly through the catheter lumen.

In some embodiments, the assembly can be configured such that the core member has a distal section and a proximal section. The distal section of the core member can be a distal tapering section. The core member can comprise a wire. For example, the distal section of the core member can comprise a distal tip. The core member distal tip can comprise polytetrafluoroethylene (PTFE or TEFLON®).

In accordance with some embodiment, a stent delivery system is provided that can comprise a catheter, a core member, a self-expanding stent, and an expandable engagement member. The catheter can have an inner wall that defines a lumen. The core member can extend within the catheter and have a distal segment.

In some embodiments, the self-expanding stent can have a length and extend along the core member distal segment radially positioned between the core member and the catheter inner wall. The expandable engagement member can be attached to the core member. The engagement member can be positioned radially between the core member and the stent and have a length less than the stent length. The engagement member can be movable to an expanded position to press the stent against the catheter inner wall and transmit axial movement of the core member to the stent for moving the stent within the catheter lumen relative to the catheter.

In some embodiments, the engagement member can comprise at least one balloon. In systems that use one or more balloons, the self-expanding stent can be positioned within the catheter and extend over the balloon. The balloon can be configured to have a first expanded state, in which the balloon presses the stent against the catheter inner wall for frictionally engaging the stent with the balloon to move the stent within the catheter lumen as the core member moves relative to the catheter.

The stent can have an axial length that is greater than an axial length of the engagement member or balloon. For example, the engagement member or balloon length can be less than about 60% of the stent length. In some systems, the engagement member or balloon length can be less than about 40% of the stent length.

For example, the balloon can be attached to the distal segment of the core member. The core member can comprise a lumen in fluid communication with the engagement member or balloon.

The engagement member can also comprise a plurality of balloons. For example, the plurality of balloons can be in fluid communication with each other.

Further, the balloon can comprise a material a durometer of less than Shore 60A. For example, the balloon can comprise a material having a durometer of from about Shore 5A to about Shore 50A or 60A. Further, the balloon can comprise a material having a durometer of from about Shore 15A to about Shore 40A. Moreover, the balloon can comprise a material having a durometer of from about Shore 20A to about Shore 30A.

The system can also have a distal structure extending proximally from the core member distal segment and interposed between an outer surface of the stent and the catheter inner wall. For example, the distal structure can comprise a coil.

In some embodiments, methods of operating a stent delivery system are also provided. A clinician can advance a distal end of a catheter in a blood vessel. Thereafter, the clinician can place the delivery system within a lumen of the catheter. The delivery system can comprise one or more of the structures or features disclosed herein. For example, the delivery system can comprise (i) a core member, (ii) a stent extending along the core member, and (iii) an engagement member radially interposed between the core member and the stent. In use, the clinician can expand the engagement member to press the stent against an inner wall of the catheter. Thereafter, the clinician can move the core member within the lumen relative to the catheter, thereby moving the stent relative to the catheter.

Movement of the core member relative to the catheter can be performed by distally advancing the core member relative to the catheter. Further, movement of the core member relative to the catheter can also be performed by proximally withdrawing the core member relative to the catheter for resheathing the stent into the catheter lumen. Proximal withdrawal of the core member can be performed after a distal end of the stent exits the distal end of the catheter.

In order to deploy the stent, some methods can also include the step of advancing the stent beyond the distal end of the catheter to allow the stent to expand into apposition with the blood vessel. Thereafter, a clinician can also expand the engagement member to a diameter larger than an inner diameter of the catheter when the engagement member is outside of the catheter lumen and within a lumen of the stent to fully expand an unexpanded portion of the stent. For example, moving the engagement member axially within the stent lumen when the engagement member is expanded to the larger diameter can facilitate fully expanding the unexpanded portion of the stent.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 2 is a cross-sectional side view of a stent delivery system having a single engagement member, according to some embodiments.

FIG. 3 is a cross-sectional side view of a stent delivery system having a plurality of engagement members, according to some embodiments.

DETAILED DESCRIPTION

Figure 1:
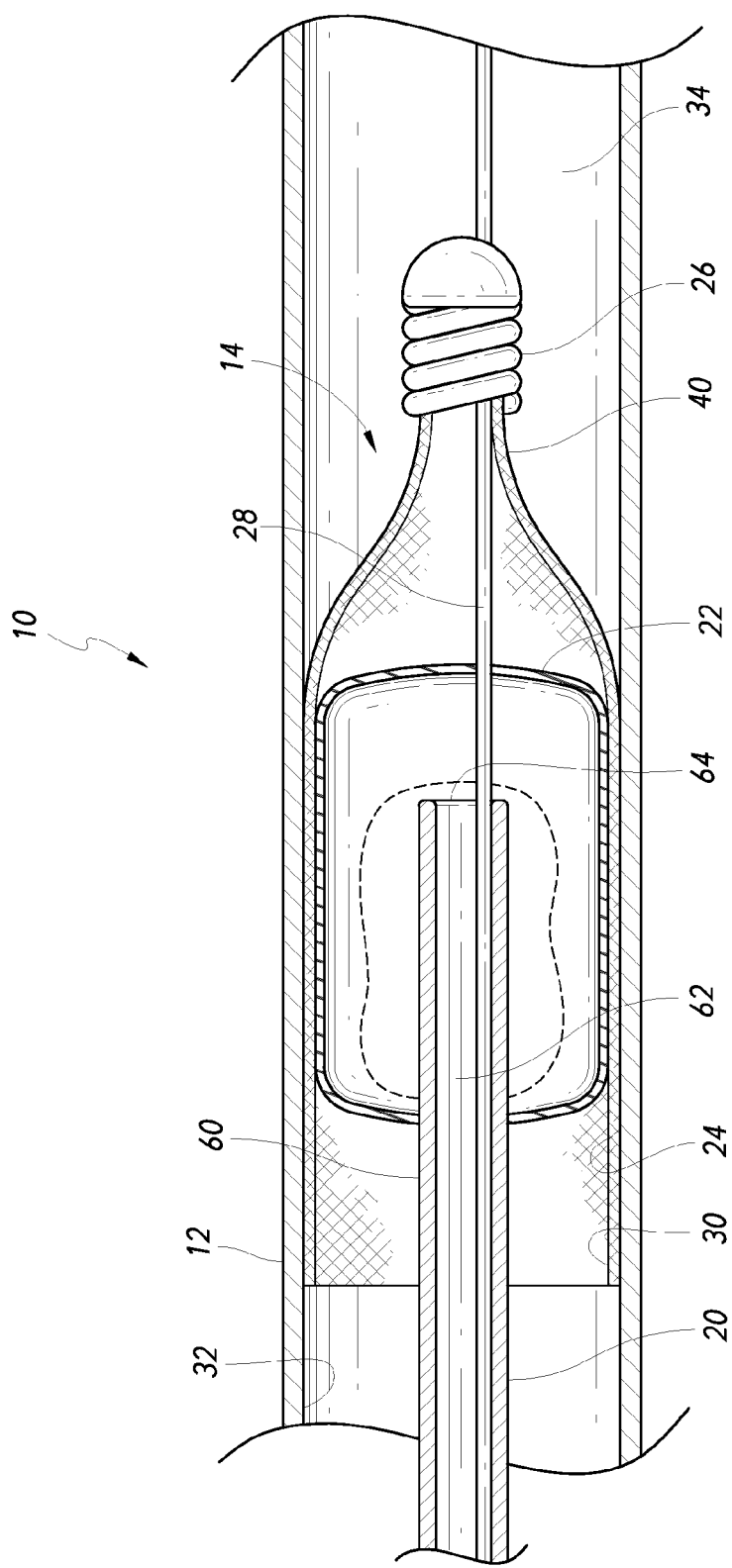
FIG. 1 is a cross-sectional side view of a stent delivery system, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Described herein are various embodiments of stent delivery systems exhibiting small cross-sections which are highly flexible and can provide advantages such as allowing the clinician to recapture, collapse, withdraw, or resheath and reposition a partially expanded stent, reduce and avoid vessel abrasions or perforations during placement, place several stents (e.g., "telescoping") without removing the catheter, and/or avoid torsional stress and "whipping" that can occur during delivery of the stent. Various other features and advantages of some embodiments are discussed and shown herein.

In some embodiments, a stent delivery system is provided that can include a core assembly and an introducer sheath and/or catheter. The system can comprise a stent extending over, or carried or supported by, a core member of the core assembly. The core member can comprise a core wire. The core assembly can be movable within the introducer sheath and/or catheter in order to deliver the stent to a predetermined treatment site, such as an aneurysm, within the vasculature of a patient. Thus, prior to delivery of the stent, the catheter can be configured to be introduced and advanced through the vasculature of the patient. The catheter can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheter or an adjacent surface with a hydrophilic material such as polyvinylpyrrolidone (PVP) or some other plastic coating. Additionally, either surface can be coated with various combinations of different materials, depending upon the desired results.

The stent can be characterized as a vascular occluding device, a revascularization device and/or an embolization device. In some embodiments, the stent can be an expandable stent made of two or more filaments. The filaments can be formed of known flexible materials including shape memory materials, such as nitinol, platinum and stainless steel. In some embodiments, the filaments can be round or ovoid wire. Further, the filaments can be configured such that the stent is self-expanding. In some embodiments, the stent can be fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer.

The wire filaments can be braided into a lattice-like structure. In at least one embodiment, during braiding or winding of the stent, the filaments can be braided using a 1-over-2-under-2 pattern. In other embodiments, however, other methods of braiding can be followed, without departing from the scope of the disclosure. The stent can exhibit a porosity configured to reduce haemodynamic flow into and/or induce thrombosis within, for example, an aneurysm, but simultaneously allow perfusion to an adjacent branch vessel whose ostium is crossed by a portion of the stent. As will be appreciated, the porosity of the stent can be adjusted by "packing" the stent during deployment, or advancing an expanding portion of the stent against an expanded portion of the stent to decrease the porosity of the stent. Likewise, the porosity can be increased by withdrawing an expanding portion of the stent from an expanded portion of the stent. The ends of the stent can be cut to length and therefore remain free for radial expansion and contraction. The stent can exhibit a high degree of flexibility due to the materials used, the density (i.e., the porosity) of the filaments, and the fact that the filament ends are not secured to each other.

Information regarding additional embodiments, features, and other details of the occlusion devices or stents, methods of use, and other components that can optionally be used or implemented in embodiments of the occlusion devices or stents described herein, can be found in Applicant's co-pending applications U.S. patent application Ser. No. 12/751,997, filed on Mar. 31, 2010; Ser. No. 12/426,560, filed on Apr. 20, 2009; Ser. No. 11/136,395, filed May 25, 2005; Ser. No. 11/420,025, filed May 24, 2006; Ser. No. 11/420,027, filed May 24, 2006; Ser. No. 12/425,604, filed Apr. 17, 2009; Ser. No. 12/896,707, filed Oct. 1, 2010; 61/483,615, filed May 6, 2011; 61/615,183, filed Mar. 23, 2012; Ser. No. 13/795,556, filed Mar. 12, 2013; Ser. No. 13/614,349, titled Methods and Apparatus for Luminal Stenting, filed on Sep. 13, 2012; Ser. No. 13/692,021, titled Methods and Apparatus for Luminal Stenting, filed on Dec. 3, 2012; and Ser. No. 13/664,547, titled Methods and Apparatus for Luminal Stenting, filed on Oct. 31, 2012; the entireties of each of which are incorporated herein by reference.

The core member can be sufficiently flexible to allow the stent delivery system to bend and conform to the curvature of the vasculature as needed for axial movement of the stent within the vasculature. The core member can be made of a conventional guidewire material and have a solid cross-section. Alternatively, the core member can be formed from a hypotube. The material used for the core member can be any of the known guidewire materials including superelastic metals or shape memory alloys, e.g., nitinol. For example, the core member, along its length or at least at its distal end or tip, can comprise a coating of polytetrafluoroethylene (PTFE or TEFLON®). Alternatively, the core member can be formed of metals such as stainless steel.

In one or more embodiments, the stent delivery system can exhibit the same degree of flexibility along its entire length. In other embodiments, however, the stent delivery system can have two or more longitudinal sections, each with differing degrees of flexibility or stiffness. The different degrees of flexibility for the stent delivery system can be created using different materials and/or thicknesses within different longitudinal sections of the core member. In another embodiment, the flexibility of the core member can be controlled by spaced cuts (not shown) formed within the core member. These cuts can be longitudinally and/or circumferentially spaced from each other.

The stent delivery system can comprise a catheter, a stent, and a core assembly having a core member extending within the catheter, and an engagement member attached to the core member. The stent can be interposed between the engagement member and an interior surface of the catheter. The engagement member can be selectively actuated by the clinician in order to provide an engagement between the stent and the core assembly, in order to move the stent within the catheter. Thus, the transmission of an axial force to the stent can be achieved by pressing the stent against the inner wall of the catheter and frictionally engaging or dragging the stent within the catheter.

In some embodiments, the engagement member(s) can have an axial length that is less than an axial length of the stent. For example, the engagement member(s) can comprise a balloon that is axially shorter than the stent, such as being less than three-quarters of the length of the stent, equal to or less than one half of the length of the stent, equal to or less than one-quarter of the length of the stent, or otherwise. Further, if multiple engagement members are used, each engagement member can define an axial length that is less than the axial length of the stent. A collective axial length of the engagement members can be greater, equal to, or less than the axial length of the stent.

For example, the engagement member can comprise a balloon that inflates within a lumen of the stent and a radially presses the stent against a lubricious inner wall of the catheter. The frictional force between the stent and the engagement member can be greater than the frictional force between the stent and the interior surface of the catheter, thereby allowing an axial force imparted to the stent through the core assembly to result in axial movement of the stent, whether distal or proximal.

Accordingly, in some embodiments, the system can deliver a self-expanding stent without the use of a proximal stop or other structure that "pushes" (e.g., by contacting and pushing a proximal end of the stent) the stent through the catheter. The system can therefore be implemented using fewer components and achieve surprising results through the simplicity and efficiency of its design. The simplicity of such a design can be advantageous at least because it requires fewer parts and lowers the risk of structural failure or degradation, as well as reducing the cost and time requirements.

The engagement between the stent and the engagement member can allow a clinician to exert a distal pushing force on the stent to distally advance the stent relative to the catheter, or to exert a proximal pulling force on the stent to proximally withdraw or retract the stent into the catheter, even after a significant portion (e.g., about 50% to about 75%) of the stent has been moved distally beyond a distal end of the catheter and expanded into apposition with a vessel wall.

In order to navigate the core assembly to the predetermined treatment site, the engagement mechanism can be actuated to engage the stent within the catheter. In some embodiments, the engagement mechanism can comprise a balloon that is inflated to a degree sufficient to press the stent against the catheter inner wall, thereby creating a frictional engagement between the stent and the core assembly. Some embodiments enable the balloon to contact the inner lumen of the stent along a portion or all of the inner circumference of the stent lumen. Further, some embodiments are configured such that the engagement mechanism comprises multiple balloons. Provided this engagement, the core assembly can be advanced through the catheter using a distally oriented force.

In some embodiments, during the navigation of the core assembly along the length of the catheter, the core assembly may encounter tortuous vessel geometries. In such situations, the engagement mechanism can be selectively actuated to add or release pressure (e.g., partially inflated or deflated) so that the engagement between the core assembly and the stent is maintained and so that the stent structure is unharmed.

After navigating the core assembly along the length of the catheter to the treatment site within the patient, the stent can be deployed from the catheter in a variety of ways. In some embodiments, the catheter can be retracted while maintaining the position of the core member to expose the distal end of the core member and the distal end of the stent. The stent can be engaged in a collapsed state at least at the distal end or portion thereof. The stent can also be engaged at both the proximal and distal ends or portions thereof when moved beyond a distal end of the catheter.

For example, the catheter can be proximally withdrawn relative to the core assembly, thereby exposing a distal tip assembly of the core assembly. The distal portion or assembly of the core assembly can comprise a distal tip structure or cover.

The distal tip structure can comprise at least one member or component that can be carried by the core member. In some embodiments, the at least one member can be oriented generally transverse or parallel to the core member. For example, the tip structure can comprise a coil(s), a circumferentially-extending band(s) of material, clamp(s), and/or other structures that can pass smoothly within a vessel at the distal portion of the core member. Further, the at least one member can comprise at least one segment of the coil or other structure.

In some embodiments, the distal structure can comprise a sheet or other portion of flexible material that, in a first, wrapping, delivery, or pre-expansion position, at least partially covers or surrounds a distal end of the stent and extends proximally therefrom, over an intermediate portion of the core assembly. For example, in this position, the core assembly can be positioned axially within the lumen of the catheter such that the distal end of the stent is positioned axially adjacent to the distal end of the catheter with at least a portion of the distal structure extending in a space within the catheter lumen radially between the distal end of the catheter and at least one of the stent or the intermediate portion of the core assembly.

The distal structure can extend proximally from the distal portion or assembly and the space between the distal portion and the catheter. Further, in some embodiments, at least a portion of the distal structure can be positioned outside of a space radially between the distal tip structure of the core assembly and the catheter. Accordingly, in some embodiments, the distal structure can comprise one or more strips of a flexible and/or lubricious material that can be positioned radially in between portions of the distal end of the stent and the inner surface of the catheter to reduce sliding friction between the core assembly and the catheter.

Some embodiments of the system can be configured such that when the distal end of the stent is unsheathed or moved beyond the distal end of the catheter lumen, the distal end of the stent remains in the unexpanded position. The distal end of the stent can later be actuated to allow the distal end of the stent to expand and thereby urge the distal structure from the first, wrapping, delivery, or pre-expansion position or configuration to a second, unfurled, expanded, resheathing, or everted position or configuration. The distal structure can move to an everted position or configuration, and the distal end of the stent can be expanded into apposition with the vessel wall.

However, in accordance with some embodiments, after the stent has been partially expanded or moved partially beyond a distal end of the catheter, the stent delivery system can allow the clinician to recapture, collapse, withdraw, or resheath the stent into the catheter and later unsheath the stent again from the catheter. As noted above, some embodiments allow the stent to be secured, grasped, or engaged by the engagement mechanism of the core assembly in order to exert a distal pushing force on the stent or to exert a proximal pulling force on the stent. Thus, even when the stent has been partially unsheathed or moved beyond a distal end of the catheter, a proximal end of the stent can remain secured, grasped, or engaged with the engagement mechanism to allow the stent to be retracted or withdrawn proximally into the catheter until the entire length of the stent has been resheathed into the catheter. Even if the stent distal end has been released from the distal structure and expanded into apposition with the vessel wall, the engagement mechanism can still function to allow the stent to be recaptured, withdrawn, or resheathed into the catheter. Thus, in some embodiments, the distal structure can be retracted or withdrawn into the catheter in a second position. If the distal structure comprises a flexible material, the second position can be achieved when the flexible material is in an unfurled, expanded, resheathing, or everted configuration.

Referring now to the figures, which illustrate some embodiments of the systems and methods disclosed herein, FIG. 1 illustrates an embodiment of a stent delivery system 10. The delivery system 10 can comprise a catheter 12 and a core assembly 14. The core assembly 14 can comprise a core member 20, at least one engagement member 22, and a stent 24. The core assembly 14 can also comprise a distal structure or cover 26.

In some embodiments, the core member 20 can comprise a reduced diameter section 28. The reduced diameter section 28 can comprise a core wire, as illustrated in FIG. 1. However, the reduced diameter section 28 can also comprise a section of the core member 20 that tapers to a reduced diameter. The reduced diameter section 28 can comprise a lumen, however, the reduced diameter section 28 can also have a solid core. The reduced diameter section 28 can comprise a flexible, elongate tip, made from a soft, pliable material such as Teflon.

The engagement member(s) 22 can be configured to selectively engage an interior surface 30 of the stent 24 and press the stent 24 against an interior surface 32 of the catheter 12. The interior surface 32 of the catheter 12 can comprise a lubricious coating or material that provides relatively low friction between the interior surface 32 and the stent 24. In an aspect of some embodiments, the friction between the engagement member(s) 22 and the surface 30 of the stent 24 will exceed the friction between the stent 24 and the catheter 12, thus allowing the stent 24 to be moved within a lumen 34 of the catheter 12 in response to movement of the core assembly 14.

As shown in FIG. 1, a distal end 40 of the stent 24 can be received within the distal structure 26. Thus, during delivery of the core assembly 14 to a treatment site, the distal end 40 of the stent 24 can be tapered into and constrained within the distal structure 26. The distal structure 26 can tend to exert a proximal pushing force on the distal end 40 of the stent 24 when the core assembly 14 is moved in a proximal direction within the catheter 12. However, in accordance with some embodiments, the distal structure 26 may exert an insubstantial or no distal pulling force on the distal end 40 of the stent 24 when the core assembly 14 is advanced distally towards the treatment site. Instead, the core assembly 14 can rely entirely on the engagement between the engagement member(s) 22 and the stent 24 in exerting a distal force on the stent 24 to cause the stent 24 to advance in the distal direction towards the treatment site. The distal structure 26 can facilitate delivery of the stent 24 to the treatment site, as well as facilitate resheathing or retrieval of the stent 24 and/or the entire core assembly 14, such as the structure disclosed in co-pending U.S. application Ser. No. 13/692,021, titled Methods and Apparatus for Luminal Stenting, filed on Dec. 3, 2012 (reference HKN-02608 (2), 080373-0377), the entirety of which is incorporated herein by reference. The resheathing of the core assembly can be done with or without the stent engaged or secured therewith.

According to some embodiments disclosed herein, the engagement member(s) 22 can be coupled to the core member 20 along a distal segment 60 thereof. The engagement member(s) 22 can extend beyond a distal end 64 of the core member 20. However, the engagement member(s) 22 can also be positioned, in whole or in part, proximally relative to the distal end 64 of the core member 20.

In some embodiments, the engagement member 22 can comprise a balloon. For example, the distal segment can comprise one or more apertures that are in fluid communication with a lumen 62 of the core member 20. The balloon engagement member can be in fluid communication with the aperture(s) and a lumen 62 of the core member 20. Accordingly, the balloon engagement member can be actuated by the clinician to selectively expand or contract the balloon, as necessary. Further, as discussed further herein, some embodiments can be provided in which a plurality of balloon engagement members are attached to the core member, in which embodiments the lumen of the core member can be in fluid communication with each of the balloon engagement members via one or more apertures.

In some embodiments in which the engagement member 22 comprises a balloon, the balloon can be much softer than that used in other prior art devices such as balloon-based stent expansion systems. Balloons in such prior art devices generally have a durometer greater than Shore 60A. However, some embodiments provided herein can use a balloon having a durometer that is about Shore 60A or less. An aspect of some embodiments disclosed herein is that by using a self-expanding stent, the balloon toughness and durometer need not be as great as that used in other devices, which required that the balloon have strength is sufficient to expand the stent. Thus, some embodiments disclosed herein can use a soft or lightweight balloon that is used in the transport or movement of the stent through the catheter as well as in the further expansion of the stent after it has been placed and self expanded into the vessel.

For example, a balloon engagement member in some embodiments can have a durometer of from about Shore 5A to about Shore 60A. Further, a balloon engagement member in some embodiments can have a durometer of from about Shore 15A to about Shore 50A. Additionally, a balloon engagement member in some embodiments can have a durometer of from about Shore 20A to about Shore 30A. In some embodiments, a balloon engagement member can have a durometer of about Shore 25A. The durometer ranges of some embodiments can therefore be much lower than those employed in the prior art and may not be sufficient to expand a balloon-expandable stent.

FIG. 2 illustrates an embodiment of a stent delivery system 100 which can be similar to any of the embodiments of the system 10 in structure, function and method of use, instead of and in addition to the following description and accompanying drawings. In this embodiment, the system 100 comprises a catheter 112, a core member 120, and engagement member 122, and a stent 124. In this embodiment, as in FIG. 1, the engagement member 122 defines an axial length 130 that is substantially less than an axial length 132 of the stent 124. The axial length 130 of the engagement member(s) 122 can be slightly less than the axial length 132 of the stent 124. However, as illustrated, some embodiments can be configured such that the axial length 130 is less than half of the axial length 132. Indeed, the engagement member axial length can be less than about 90% of the stent axial length. However, the engagement member axial length can be less than about 80%, 70%, 60%, 50%, 40%, 30%, 20%, or 10% of the stent axial length. Furthermore, in some embodiments, the engagement member axial length 130 can be equal to or greater than a radius 134 of the engagement member 122.

The core assembly can comprise one or more engagement members. FIGS. 1 and 2 illustrate core assemblies having a single engagement member. However, FIG. 3 illustrates an embodiment of a stent delivery system 150 having a catheter 162, a core member 170, a stent 174, and first and second engagement members 176, 178. The system 150 can be similar to any of the embodiments of the system 10 in structure, function and method of use, instead of and in addition to the following description and accompanying drawings. The first and second engagement members 176, 178 can be attached to a distal segment of the core member 170. In some embodiments, the first and second engagement members 176, 178 can be positioned adjacent to each other, while in some embodiments the first and second engagement members 176, 178 can be axially spaced apart from each other along the core member 170.

As illustrated in FIG. 3, the first and second engagement members 176, 178 can be in a close axial spacing and in fluid communication with a lumen of the core member 170. Accordingly, the first and second engagement members 176, 178 can comprise balloons that are actuatable to expand or contract the balloons. While the first and second engagement members 176, 178 can be actuated simultaneously using a single fluid lumen (such as that illustrated in FIG. 3), some embodiments can comprise a plurality of independent lumens that fluidly communicate with the engagement members on an individual basis to allow selective, independent control of each of the engagement members.

Additionally, in some embodiments having a plurality of engagement members, the engagement members can have different or identical configurations. For example, as illustrated, the first engagement member 176 can be positioned proximally relative to the second engagement member 178 and comprise a generally annular shape. Further, the second engagement member 178 can be positioned distally relative to the first engagement member 176 and extend axially beyond a distal end 180 of the core member 170. Further, as illustrated, the axial length of the second engagement member 178 can be greater than the axial length of the first engagement member 176.

In embodiments with multiple engagement members, the compliance of the engagement members, such as hardness, rigidity, or stiffness, or the softness, deflectability, or deformability, can be modified to affect and the resheathability and/or the maneuverability or pushability of the device. The engagement members can have similar or different compliances. Generally, when a more compliant (softer, more deflectable, or more deformable) material is used, the pushability and maneuverability of the assembly can be improved without much benefit to the resheathability. Conversely, generally, when a less compliant (harder, more rigid, or more stiff) material is used, the pushability and maneuverability of the assembly can be decreased, but the resheathability can improve.

For example, the first and second engagement members 176, 178 can each have a hardness that is about equal. However, in some embodiments, the first and second engagement members 176, 178 can each have a hardness that is different. The second or distal engagement member 176 can have a greater hardness than the first or proximal engagement member 178. Alternatively, the first or proximal engagement member 178 can have a greater hardness than the second or distal engagement member 176. The difference in hardness and the relative size of the engagement members can provide some advantages, such as improving the ability to resheath the stent 174.

For example, some embodiments provide that a first hardness of the first engagement member 176 is greater than a second hardness of the second engagement member 178 while both engagement members 176, 178 have a hardness less than or equal to about Shore 60A. For example, the first engagement member 176 can have a hardness of from about Shore 30A to about Shore 60A, and the second engagement member 178 can have a hardness below the hardness of the first engagement member 176 and in the range of from about Shore 10A to about Shore 50A. Specifically, in some embodiments, the first engagement member 176 can have a hardness of about Shore 60A, and the second engagement member 178 can have a hardness of about Shore 30A. Further, in some embodiments, the first engagement member 176 can have a hardness of about Shore 50A, and the second engagement member 178 can have a hardness of about Shore 30A. The difference in hardness between the first engagement member 176 and the second engagement member 178 can be less than from about 30 to about 50 durometers on Shore Hardness Scale A.

A difference between the hardness of the first and second engagement members 176, 178 can provide articulation between the first and second engagement members 176, 178 when advancing the stent 174 within the catheter 162. Additionally, the hardness difference can also provide a sufficiently rigid structure to facilitate recapturing or resheathing of the stent 174 while optimizing pushability or maneuverability of the members 176, 178.

For example, some embodiments can have a proximal or first engagement member that is harder than a distal or second engagement member. The proximal or first engagement member can have a smaller axial length than the relatively soft distal or second engagement member. In such embodiments, the majority of the core assembly can demonstrate excellent pushability, flexibility, or maneuverability during advancement due to the majority presence of the softer distal or second engagement member while still demonstrating excellent recapturability or resheathability because of the presence of the harder proximal or first engagement member. Together then, the engagement members can provide sufficient radial strength to engage and facilitate advancement of the stent through the catheter lumen while balancing the need for pushability, flexibility, and maneuverability against the need for recapturability and resheathability.

Accordingly, in some embodiments, the pushability or maneuverability of the assembly can be optimized by increasing the axial length of the relatively soft distal or second engagement member relative to the axial length of the relatively hard proximal or first engagement member. For example, in some embodiments, the ratio of the axial length of the second engagement member to the first engagement member can be from about 10 to about 1, about 8 to about 1, about 7 to about 1, about 6 to about 1, about 5 to about 1, about 4 to about 1, about 3 to about 1, about 2 to about 1, about 3 to about 2, about 4 to about 3, or about 5 to about 4.

Figure 5:
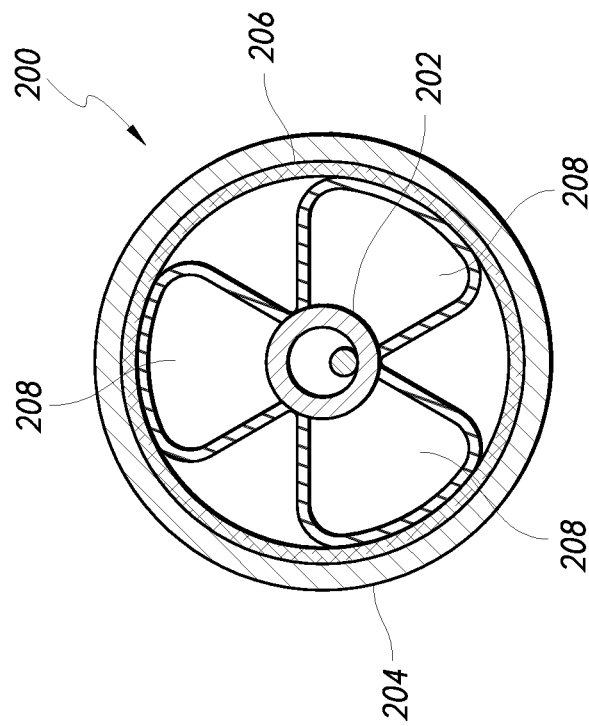
FIG. 5 is a cross-sectional end view illustrating a cross-sectional profile of a engagement member, according to some embodiments.
Figure 4:
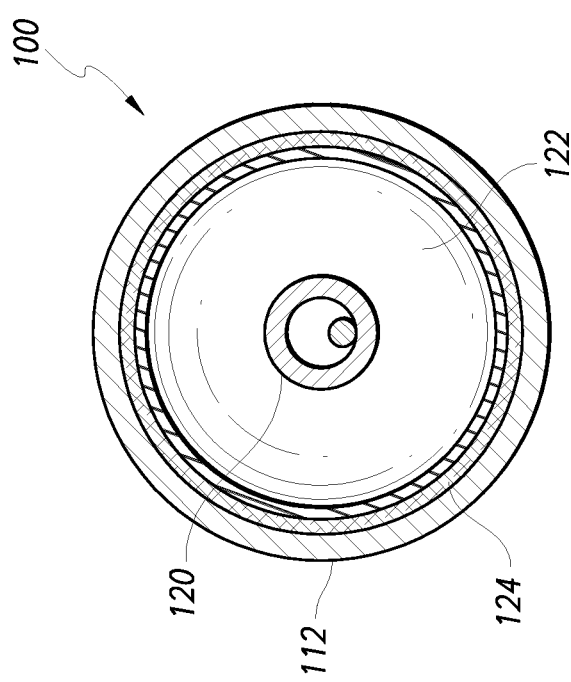
FIG. 4 is a cross-sectional end view illustrating a cross-sectional profile of a engagement member, according to some embodiments.

Referring to FIGS. 4 and 5, alternative embodiments of core assemblies are illustrated in cross-sectional views taken along the longitudinal axis of the system. In FIG. 4, the stent delivery system 100 is illustrated in which the engagement member 122 has a generally circular cross-sectional configuration. Thus, the engagement member 122 can comprise a generally annular balloon that extends circumferentially about the core member 120.

FIG. 5 illustrates a cross-sectional view of an alternative embodiment in which a stent delivery system 200 comprises a core member 202, a catheter 204, a stent 206, and a plurality of engagement members 208. The system 200 can be similar to any of the embodiments of the system 10 in structure, function and method of use, instead of and in addition to the following description and accompanying drawings. As shown, the engagement members 208 can extend about at least a portion of the circumference of the core member 202. However, in contrast to other embodiments, the engagement members 208 extend discontinuously about the circumference of the core member 202. As illustrated, the system 200 can be configured to comprise three engagement members 208. However, some embodiments can comprise more or less than three engagement members. Additionally, the engagement members 208 can extend axially along the core member 202 such that the engagement members 208 comprise generally elongate members. Furthermore, the engagement members 208 can be simultaneously or independently actuatable. Thus, the clinician can selectively control the size or expansion of all of the engagement members 208 together or separately, as necessary.

Accordingly, some embodiments disclosed herein (including those shown in FIG. 3 and FIG. 5) provide a stent delivery system that can comprise one or more engagement members that can allow a clinician to selectively adjust the size or expansion of the engagement member(s) in the radial and/or axial direction.

FIGS. 6-13 illustrate aspects of the system and methods of its use. As previously illustrated and discussed in FIG. 1, the stent 24 can be delivered to a treatment site by transmitting a distal pushing force to the stent 24 using the core assembly 14, such that the stent 24 slides within the catheter 12 until reaching the treatment site. FIGS. 6-13 illustrate not only the placement of the stent within the vessel, but also illustrate other useful aspects of the system and methods.

As illustrated and discussed herein, some embodiments can be implemented such that the engagement member (e.g., a balloon engagement member) can have a dual purpose or multiple functions: the engagement member can be used to aid in advancing the stent through the catheter by creating an engagement between the stent and the core assembly, and optionally, the engagement member can also be used to make sure that the stent is fully open after the stent is expanded into apposition with the blood vessel by being expanded within the stent lumen and used to "iron," "brush," or otherwise press against the interior surface of the stent and thereby further urge the stent into appostion with the vessel wall.

This highly useful dual purpose or multifunction aspect of some embodiments can advantageously minimize the number of components and steps used in the system and its methods of use. Particularly, some embodiments can allow a clinician or hospital to avoid the cost and procedural time of inserting a balloon guide catheter after placement of the stent 24, and using the balloon guide catheter to perform the "ironing" or "brushing" function described above. Indeed, some embodiments disclosed herein can provide significant advantages over prior systems and methods which required multiple steps and multiple delivery assemblies.

Figure 6:
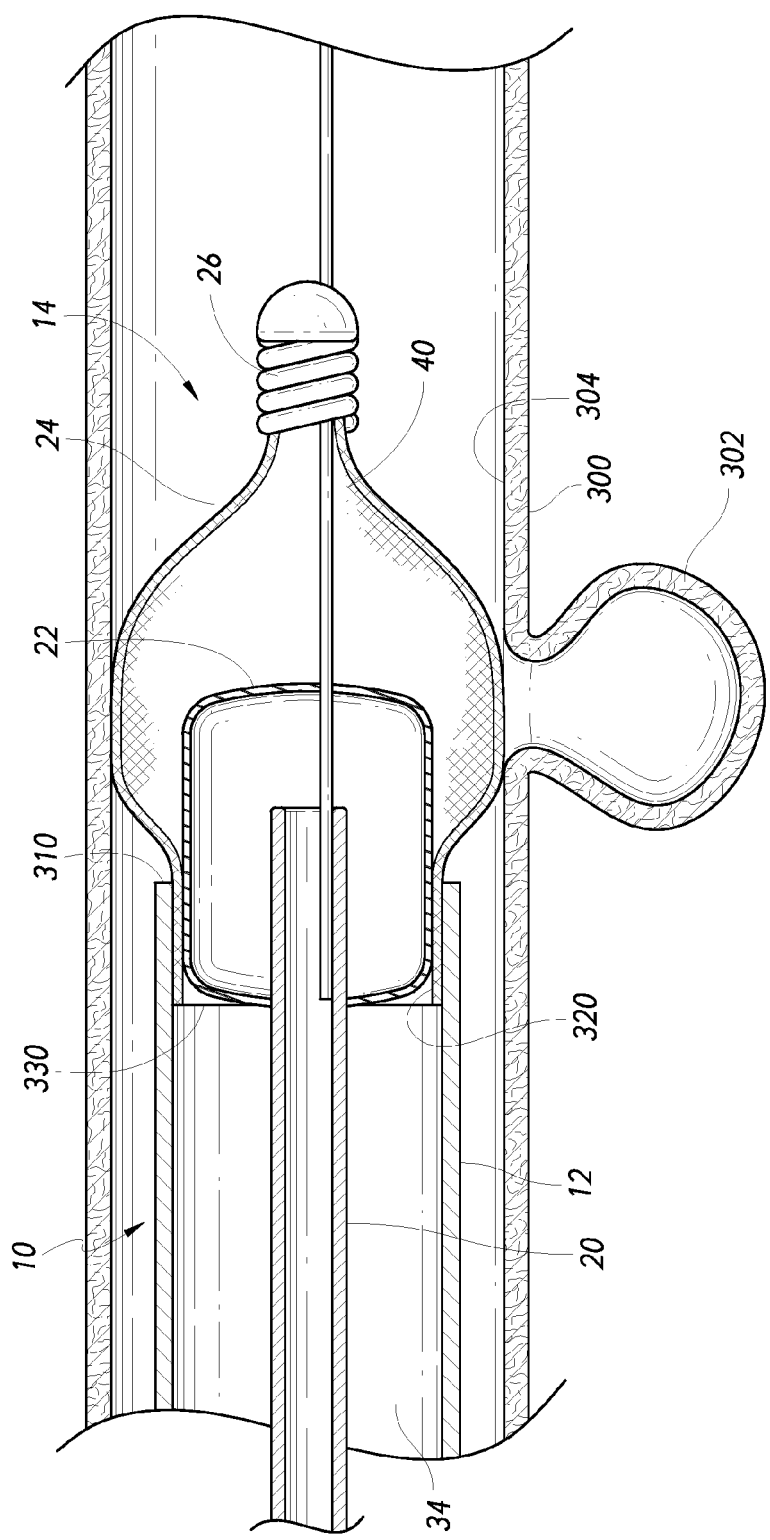
FIG. 6 is a cross-sectional side view of a stent delivery system as a stent exits a catheter of the system, according to some embodiments.

FIG. 6 illustrates the system 10 placed within a blood vessel 300. The vessel 300 can have a vessel wall 304 and a condition, such as an aneurysm 302, which is targeted for treatment by the system 10. After the system 10 has been placed at the treatment site, the core assembly 14 can be advanced relative to the catheter 12 until the core assembly 14 begins to exit a distal end 310 of the catheter 12. For example, the catheter 12 can be proximally withdrawn relative to the core assembly 14 after the stent 24 has been axially located adjacent to the aneurysm 302.

As the stent 24 exits the distal end 310 of the catheter 12, the stent 24 can begin to expand into apposition with the vessel wall 304. As illustrated in FIG. 6, during this initial positioning of the stent 24 within the vessel 300, the distal end 40 of the stent 24 can remain engaged with the distal structure 26 of the core assembly 14. Further, a segment 320 of the stent 24, such as a proximal or medial segment thereof, can remain frictionally engaged with the engagement member 22.

FIG. 6 illustrates a state of the system in which continued engagement between the stent segment 320 and the engagement member 22 can allow the clinician to retract, recapture, or resheath the stent 24 into the catheter 12, if necessary. The clinician, in order to do so, proximally withdraws the core member 20 into the catheter 12, which withdraws the engagement member 22 proximally. The engagement between the engagement member 22 and the stent segment 320 provides a proximally oriented force on the stent 24, pulling the stent 24 back into the lumen 34 of the catheter 12.

In some embodiments, upon partial exiting from the catheter lumen 34, the engagement member(s) can be slightly expanded or inflated, such as with a balloon(s). The slight expansion or inflation can occur automatically when radially unrestrained through, for example, shape memory materials that provide a radial expansion force or manually performed by the clinician. As a result, the engagement member(s) or balloon(s) can have a variable outer dimension that increases in a transition zone that is formed as the engagement member(s) or balloon(s) are advanced distally beyond the catheter distal end 310. This slight dimensional increase at the transition zone can advantageously create additional interference, traction, or friction that can enhance engagement between the engagement member(s) or balloon(s) and the stent segment 320 during initial recapturing, retraction, or resheathing of the stent 24. As the stent 24 is progressively recaptured, retracted, or resheathed, the radial expansion force, tension, or pressure within the engagement member(s) or balloon(s) can be automatically or manually reduced, if necessary.

Additionally, in embodiments that use multiple engagement members (such as multiple balloons), the radial expansion force of the individual engagement members can be automatically or manually adjusted to achieve the advantageous properties discussed above.

In some embodiments, while the stent segment 320 remains frictionally engaged with the engagement member 22, the stent distal end 40 can be released or disengaged from the distal structure 26 to allow the stent distal end 40 to expand into apposition with the vessel wall 304. This can allow the clinician to initially land the stent distal end 40 and thereafter verify proper placement of the stent before fully releasing or expanding the stent segment 320.

Some embodiments can be configured such that the engagement member(s) is rotatable relative to the distal structure. For example, in FIG. 6, the distal structure 26 can be configured to rotate relative to the engagement member 22. Thus, in embodiments where the distal structure 26 is operative to disengage or release from the stent distal end 40 by rotation, the engagement member 22 can remain engaged with the stent segment 320 while rotating the distal structure 26, which can facilitate disengagement and expansion of the stent distal end 40.

In some embodiments, the engagement member(s) and the distal structure can be rotationally fixed relative to each other using a locking mechanism on the proximal actuator. For example, when the locking mechanism is locked, the engagement member(s) and the distal structure can be rotationally fixed relative to each other. However, the engagement member(s) and the distal structure can rotate relative to each other when the locking mechanism is unlocked. In some embodiments, the distal structure can be coupled to a wire or nanotube that is actuatable by a user and is separate from the core member 20. These structures can be interconnected via the proximal actuator to facilitate rotational locking between these structures.

In some embodiments in which the engagement member 22 comprises a balloon structure or other highly compliant material, the clinician can actuate the engagement member 22 to increase the engagement pressure of the engagement member 22 with the segment 320 of the stent 24. For example, the clinician can increase the operating pressure of a balloon engagement member in order to compensate for any pressure differential between the distal and proximal portions of the balloon engagement member that may occur as the balloon engagement member is exiting the lumen 34 of the catheter 12. Thus, the system can be adjustable in order to compensate should a distal portion of the balloon engagement member tend to expand as it exits the catheter lumen 34 and thereby decrease the compressive force exerted by a proximal portion of the balloon engagement member against the interior surface of the stent within the catheter lumen 34.

Accordingly, the engagement member 22 can continue to be engaged with the stent 24 until a proximal end 330 of the stent 24 exits the distal end 310 of the catheter 12. Prior to releasing the proximal end 330 of the stent 24, some embodiments can also advantageously enable a clinician to recapture, collapse, withdraw, or resheath the stent 24 within the catheter lumen 34 at the stage such as that illustrated in FIG. 6, even after the stent 24 has been at least partially exposed or moved distally beyond the distal end 310 of the catheter 12. The stent 24 can be completely recaptured or withdrawn into the catheter lumen 34 and the system 10 can be moved within the vessel 300 or the core assembly 14 can be completely withdrawn from the catheter 12, should the need arise. Thus, the clinician can maintain control of the placement and release of the stent using the engagement member 22 in order to allow the clinician to improve the placement of the stent within the vessel 300. Once the clinician determines that the placement of the system 10 within the vessel is appropriate, the clinician can then proceed to unsheath the stent 24 by retracting the catheter 12 until the proximal end 330 of the stent 24 exits the catheter lumen 34.

Figure 7:
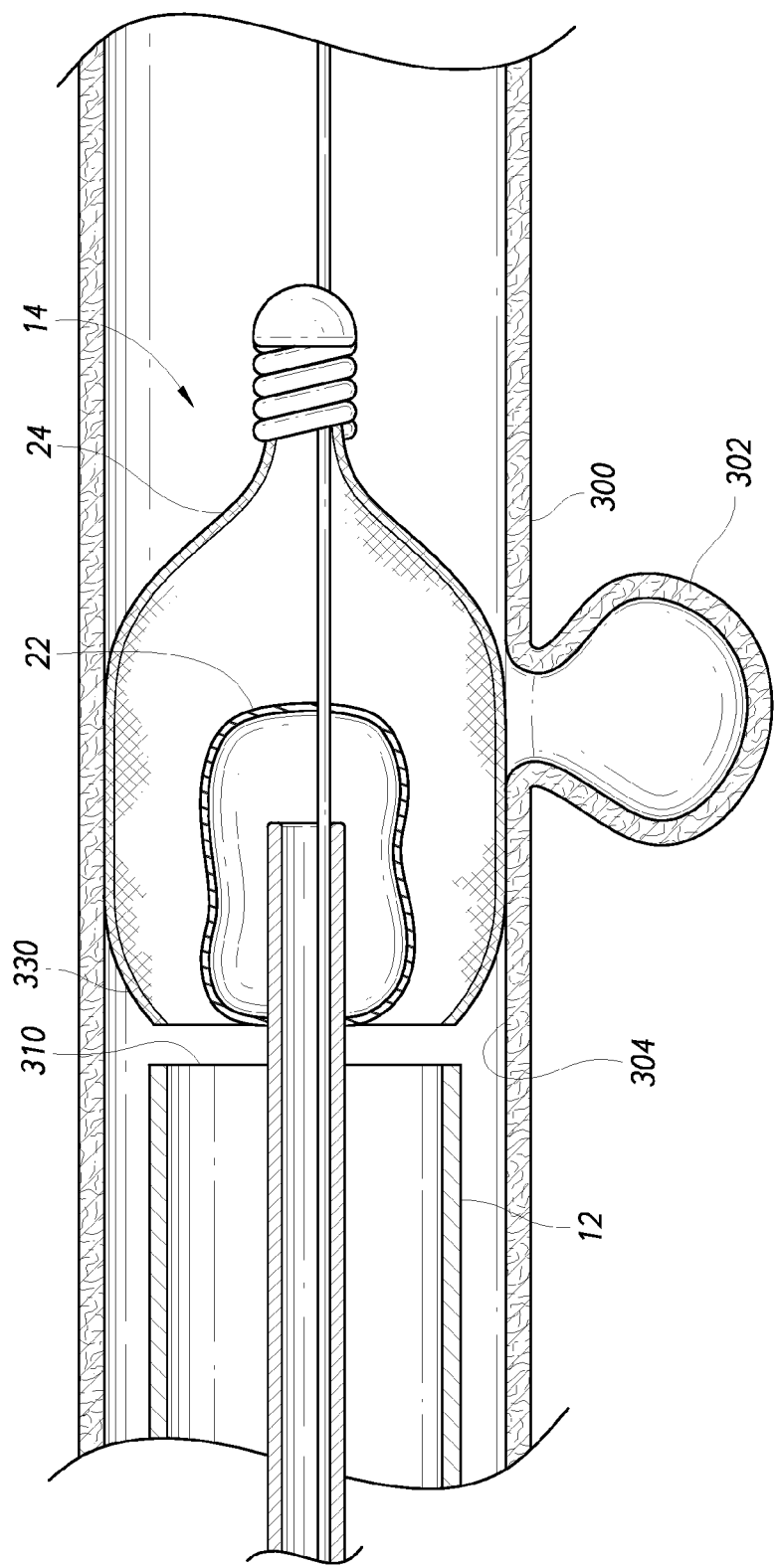
FIG. 7 is a cross-sectional side view of the stent delivery system, wherein the stent has exited the catheter, according to some embodiments.
Figure 8:
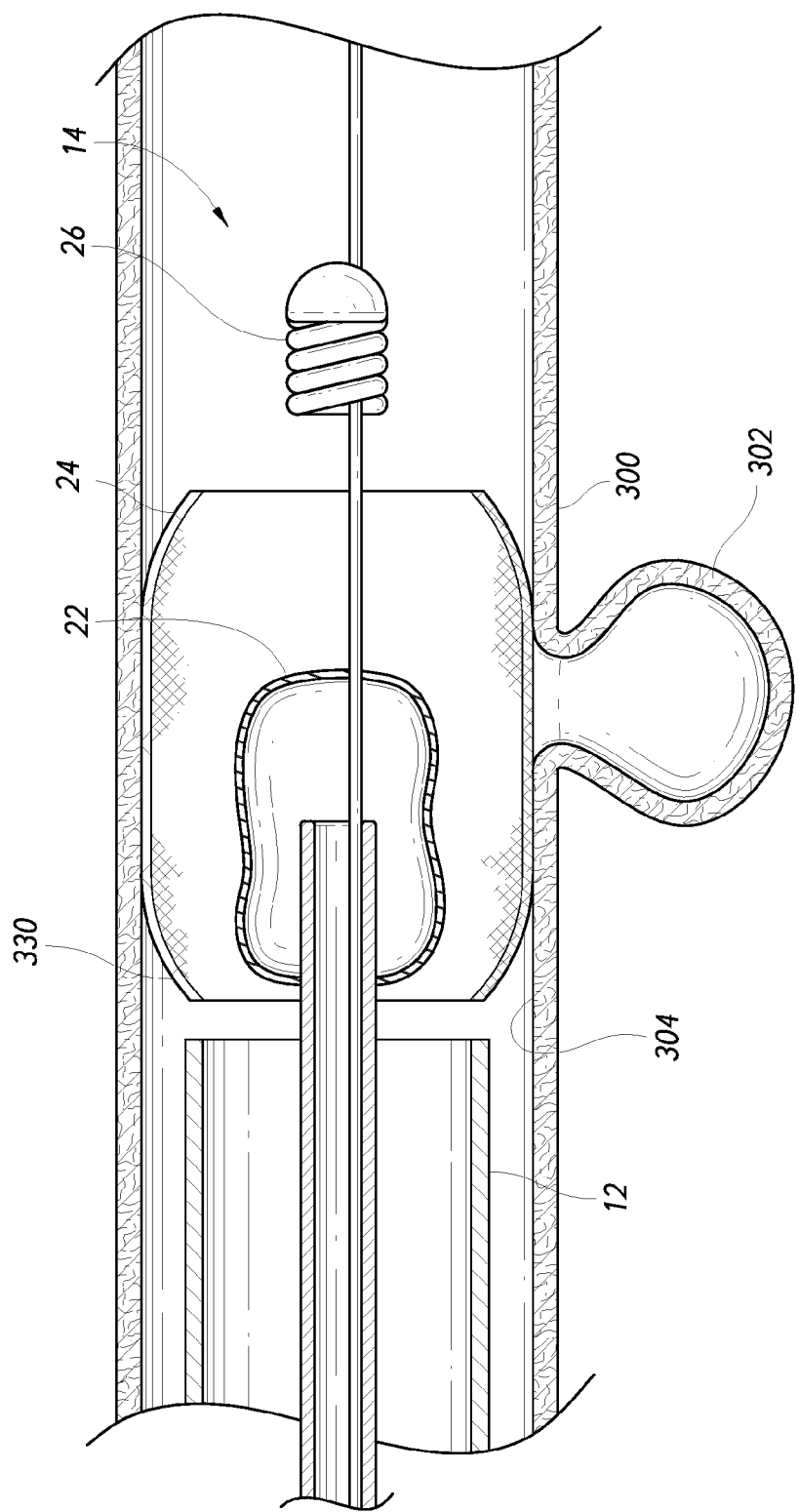
FIG. 8 is a cross-sectional side view of the stent delivery system, wherein the stent has been released from a distal structure, according to some embodiments.

After the stent proximal end 330 exits the catheter 12, the proximal end 330 can tend to expand into apposition with the vessel wall 304, as illustrated in FIG. 7. Further, when the stent proximal end 330 is released from the catheter 12, the distal end 40 can also be released from engagement with the distal structure 26. For example, the distal end 40 can be released by moving or rotating the distal structure (e.g., a coil) and pushing the distal structure (e.g., a coil) distally, whereupon the foreshortening of the expanding stent disengages the stent from the distal structure 26, as disclosed in co-pending U.S. application Ser. No. 11/420,023, titled System and Method For Delivering and Deploying an Occluding Device Within a Vessel, filed on May 24, 2006, U.S. application Ser. No. 12/426,560, titled System and Method For Delivering and Deploying an Occluding Device Within a Vessel, filed on Apr. 20, 2009, and/or U.S. application Ser. No. 13/692,021, titled Methods and Apparatus for Luminal Stenting, filed on Dec. 3, 2012 (reference HKN-02608 (2), 080373-0377), the entireties of the disclosures of which being incorporated herein by reference. Upon release of the distal end of the stent 24, the system 10 can take on the configuration shown in FIG. 8.

Figure 9:
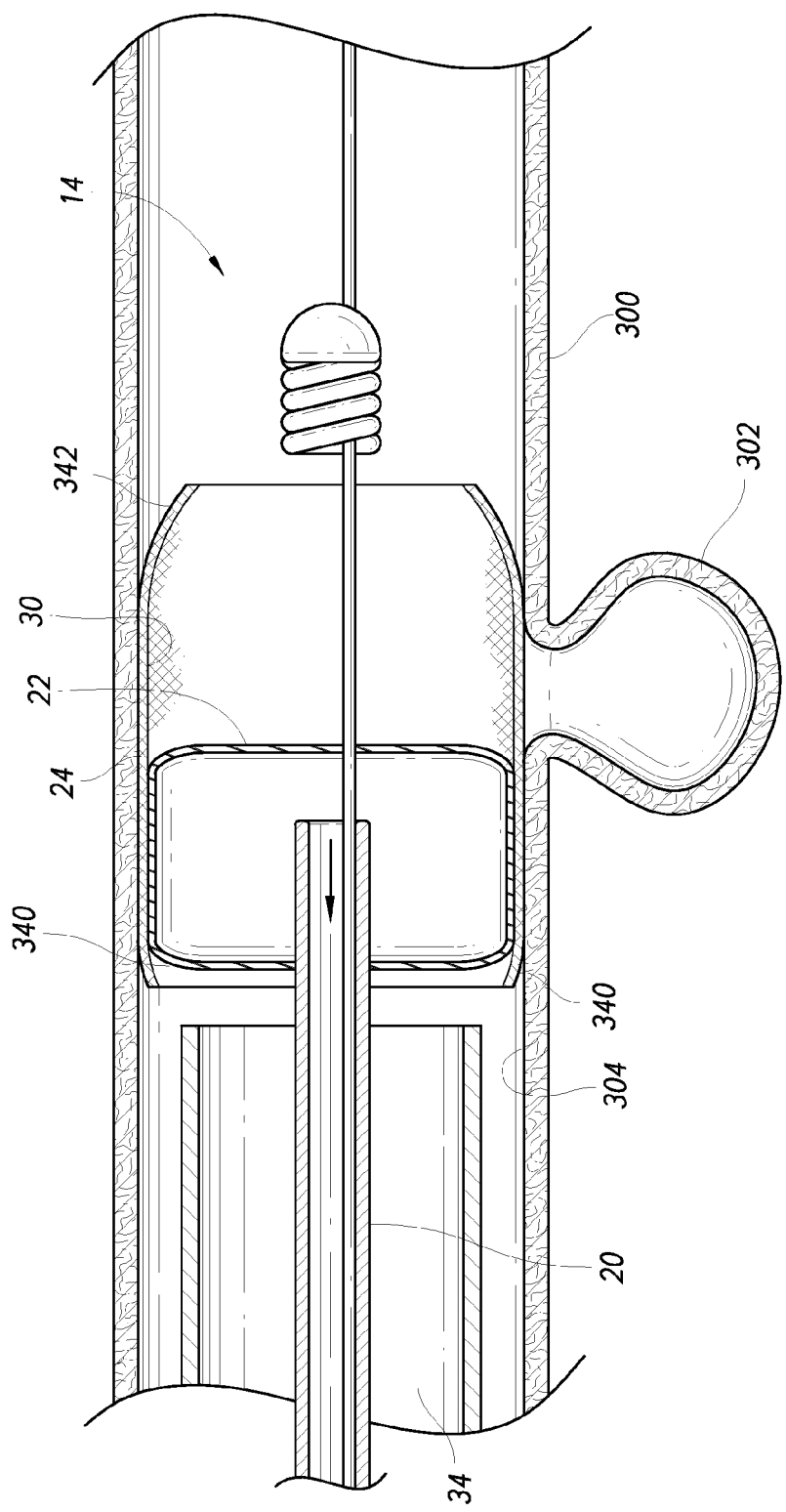
FIGS. 9-11 are cross-sectional side views of the stent delivery system, wherein the engagement member has been inflated to facilitate full expansion of the stent into apposition with a vessel wall, according to some embodiments.
Figure 10:
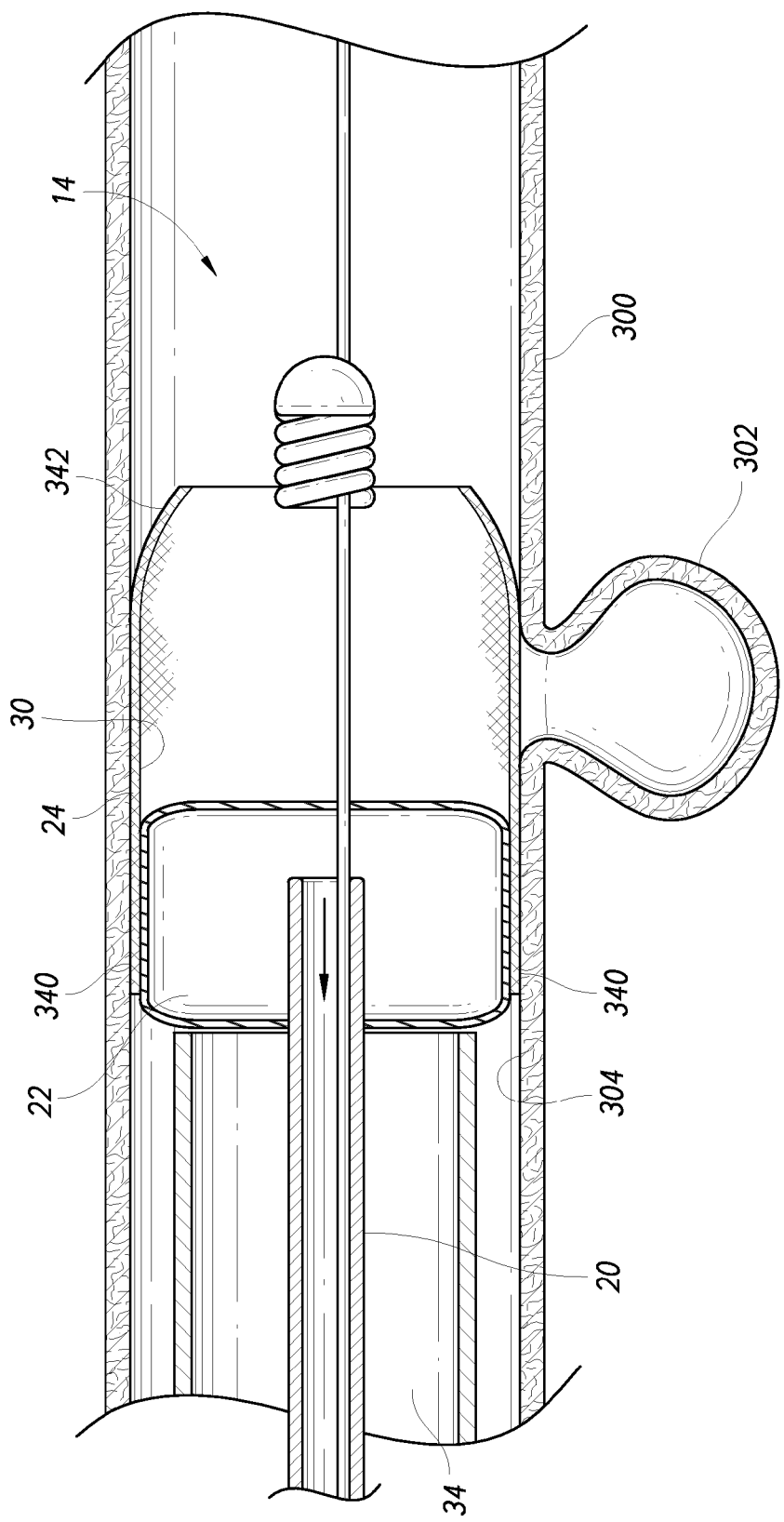
Figure 11:
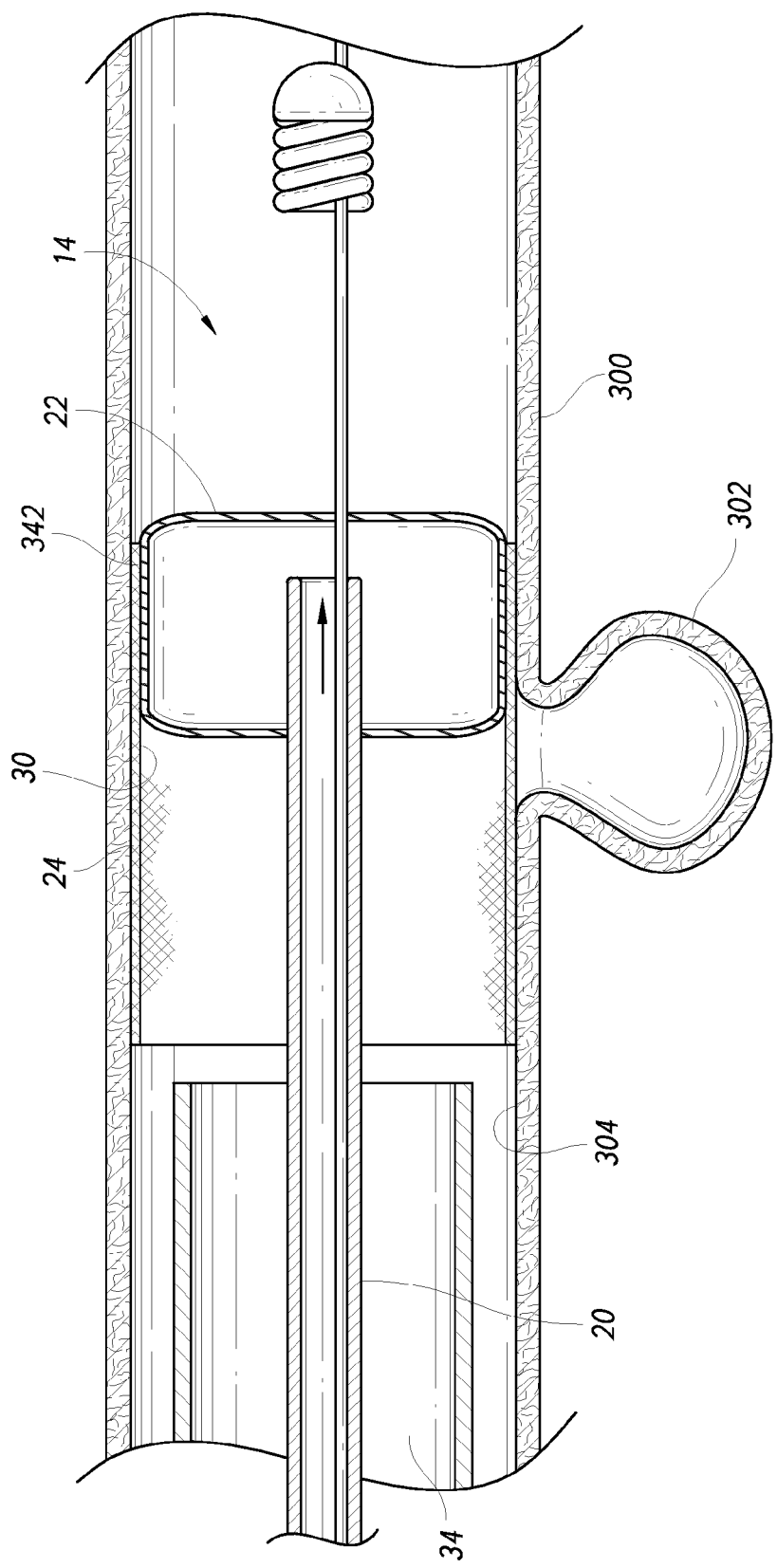

FIGS. 9-11 illustrate additional aspects of some embodiments of the system and method disclosed herein. During placement of a stent, it is often possible that the stent remain only partially open along certain segments of its length, which means that the stent may not be in contact with the walls of the vessel as desired. This is referred to as a "lazy opening" (see sections 340, 342 in FIG. 9). If this condition is left unaddressed, the stent can migrate after placement. In order to ensure that the stent has achieved proper apposition with the vessel wall, and to avoid problems such as stent misplacement or migration within the vessel, some embodiments disclosed herein allow the clinician to move the engagement member within the lumen of the stent in order to force open any segments of the stent that may remain partially expanded.

According to some embodiments, an engagement member can be expanded when positioned outside of the catheter lumen such that the engagement member can be used to "paint open," "smooth out," or facilitate complete expansion of the stent into apposition with a sidewall of the blood vessel. This advantageous function can be performed by either first expanding the engagement member and then moving the engagement member within the stent lumen. As the engagement member abuts or engages an inner surface of the stent, a force can be applied by the engagement member against the inner surface of the stent, urging the stent into a fully expanded configuration. The engagement member can first be moved within the stent lumen to a location where the stent is not fully expanded, and then the engagement member can be expanded to engage an inner surface of the stent to urge the stent to its fully expanded configuration at that location.

For example, as shown in FIG. 9, the engagement member 22 can be actuated to achieve a fully expanded, or second expanded position, when positioned outside of the catheter lumen 34. Thus, although the engagement member 22 had achieved a first expanded position within the catheter 12, the second expanded position can be achieved when the engagement member 22 is expanded to a larger radial dimension. As noted above, some embodiments can comprise a balloon engagement member, and in such embodiments, the second expanded position can provide a generally annular expanded shape which can be expanded into contact with the interior surface 30 of the stent 24 after the stent 24 is released into the vessel 300.

After the engagement member 22 is actuated to the fully or second expanded position, the core assembly 14 and engagement member 22 can be moved axially within the lumen of the stent 24 in order to urge the stent to its fully open configuration.

As shown in FIG. 10, the core assembly 14 can be moved in a proximal direction (relative to the position shown in FIG. 9) in order to cause the engagement member 22 to contact the sections 340 of the stent 24, thus causing the sections 340 to be placed into apposition with the vessel wall 304. Should additional increase in the size of the engagement member 22 be required, the clinician can actuate the engagement member 22 to provide the necessary increase, e.g., via increased fluid pressure. Accordingly, through one or more passes within the stent lumen, the sections 340 of the stent 24 can be fully expanded.

Similarly, FIG. 11 illustrates that the core assembly 14 has been advanced in a distal direction in order to cause the engagement member 22 to contact section 342 of the stent 24, thus causing the section 342 to the fully expanded into apposition with the vessel wall 304. As discussed above with regard to FIG. 10, the engagement member 22 can be inflated or deflated and moved back and forth within the stent lumen as required in order to ensure that the section 342 is properly expanded against the vessel wall 304.

Accordingly, in addition to providing advantageous pushability and resheathability, some embodiments disclosed herein can also allow the clinician to smooth out or urge outward the stent after the stent is released in order to ensure that the stent is fully expanded into apposition with the blood vessel wall.

Figure 12:
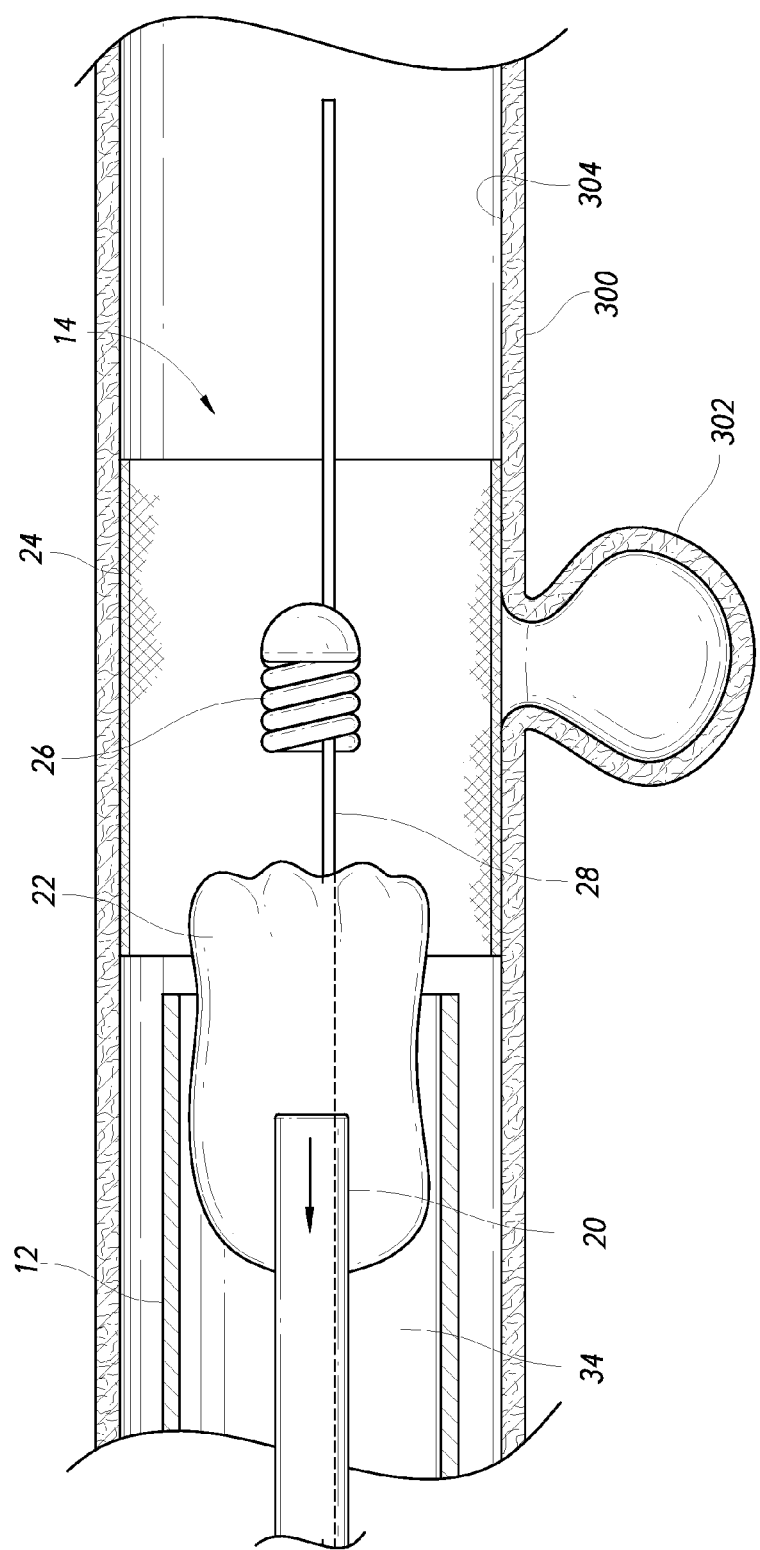
FIG. 12 is a cross-sectional side view of the stent delivery system, wherein the engagement member is withdrawn into the catheter after placement of the stent, according to some embodiments.

FIG. 12 illustrates the retrieval or withdrawal of the core assembly 14 into the catheter lumen after the stent 24 has been placed within the vessel 300. As illustrated, the core member 20 can be pulled in a proximal direction after the engagement member 22 has been actuated to an unexpanded or withdrawal position, thereby allowing the engagement member 22 to be received within the catheter lumen 34.

Figure 13:
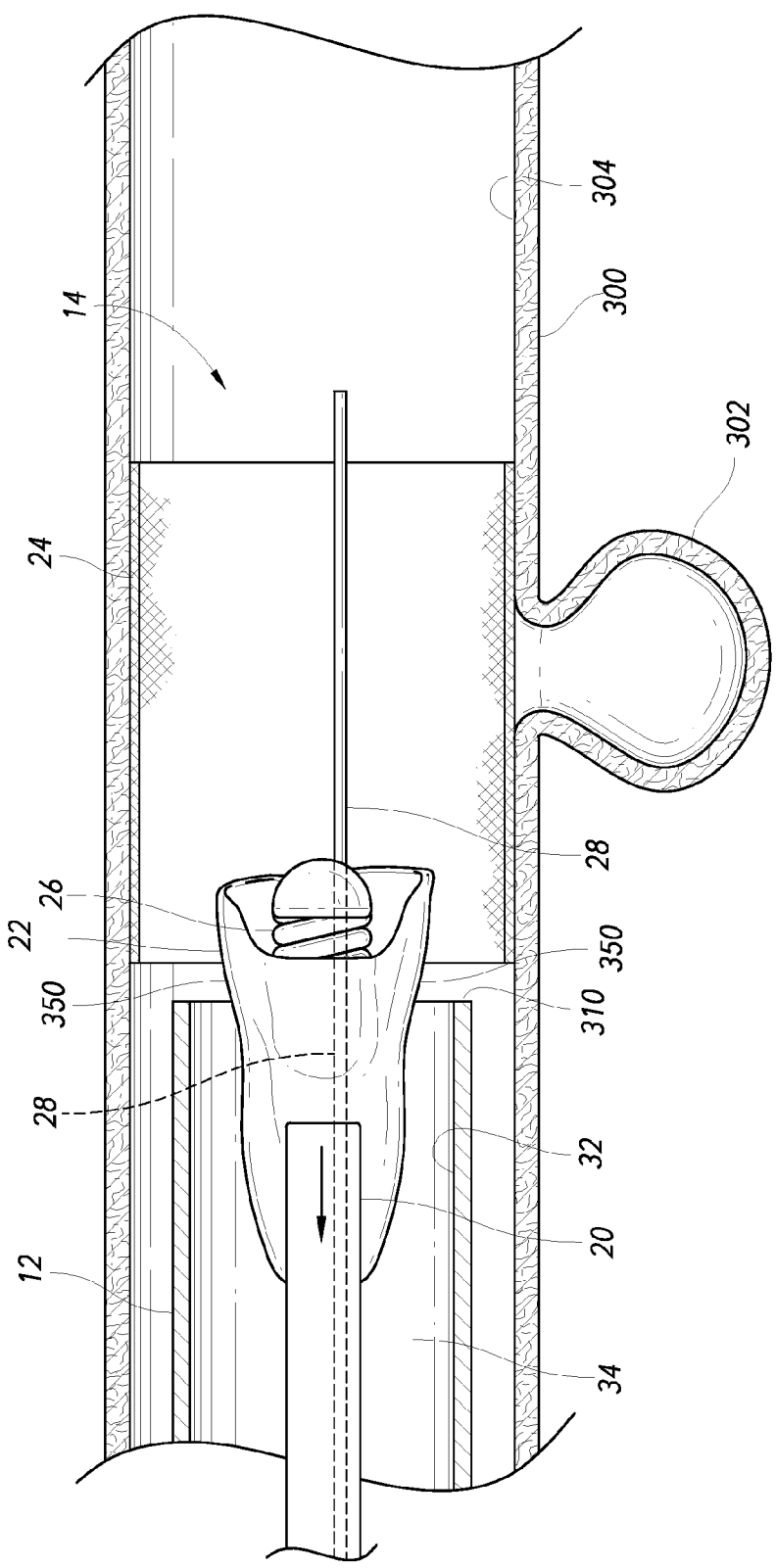
FIG. 13 is a cross-sectional side view of a stent delivery system, wherein the engagement member envelops the distal structure during withdrawal of the engagement member into the catheter, according to some embodiments.

In some embodiments, the system can be configured to facilitate recapture of the distal structure 26 when withdrawing the core assembly 14 into the catheter 12. In an aspect of such embodiments, the engagement member 22 can be actuated to an unexpanded or withdrawal position in which the engagement member 22 can extend distally to enclose or enshroud the distal structure 26, as shown in FIG. 13.

For example, in some embodiments in which the engagement member 22 is a balloon, the balloon can be deflated and assume a flexible, sheet-like state in which the natural blood flow through the vessel 300 can tend to cause the engagement member 22 to fold around or enclose the distal structure 26. Lateral sections 350 of the engagement member 22 can then act as a means for preventing the distal structure 26 from catching or snagging on the lip or distal end 310 of the catheter 12 as the core assembly 14 is withdrawn into the catheter lumen 34.

Thus, should the core assembly 14 be in direct contact with or urged against the interior surface 32 of the catheter 12 (e.g., due to sharp turns in the catheter, etc.), and specifically, at the catheter distal end 310, snagging is unlikely at the transition between the core member 20 and the engagement member 22 as the core assembly 14 is drawn into the catheter lumen 34. However, if the core assembly 14 does not have a smooth transition from the reduced diameter portion 28 to the distal structure 26, the proximal end of the distal structure 26 may tend to snag or catch on the distal end 310 of the catheter 12. Accordingly, in such situations, in order to avoid snagging, the engagement member 22 can enclose or enshroud the distal structure 26, thereby minimizing or eliminating the abrupt transition between the reduced diameter portion 28 and the distal structure 26. The system can be modified to adjust the size or material of the engagement member 22 and/or the spacing of the engagement member 22 relative to the distal structure 26, in order to enable the engagement member 22 to enclose or enshroud the distal structure 26. The minimization or elimination of the abrupt transition can tend to allow the distal structure 26 to be withdrawn into the catheter lumen 34 in a smooth, controlled manner without requiring the core assembly 14 to be rotated or jostled during recapture of the core assembly 14 into the catheter lumen 34.

Figure 14:
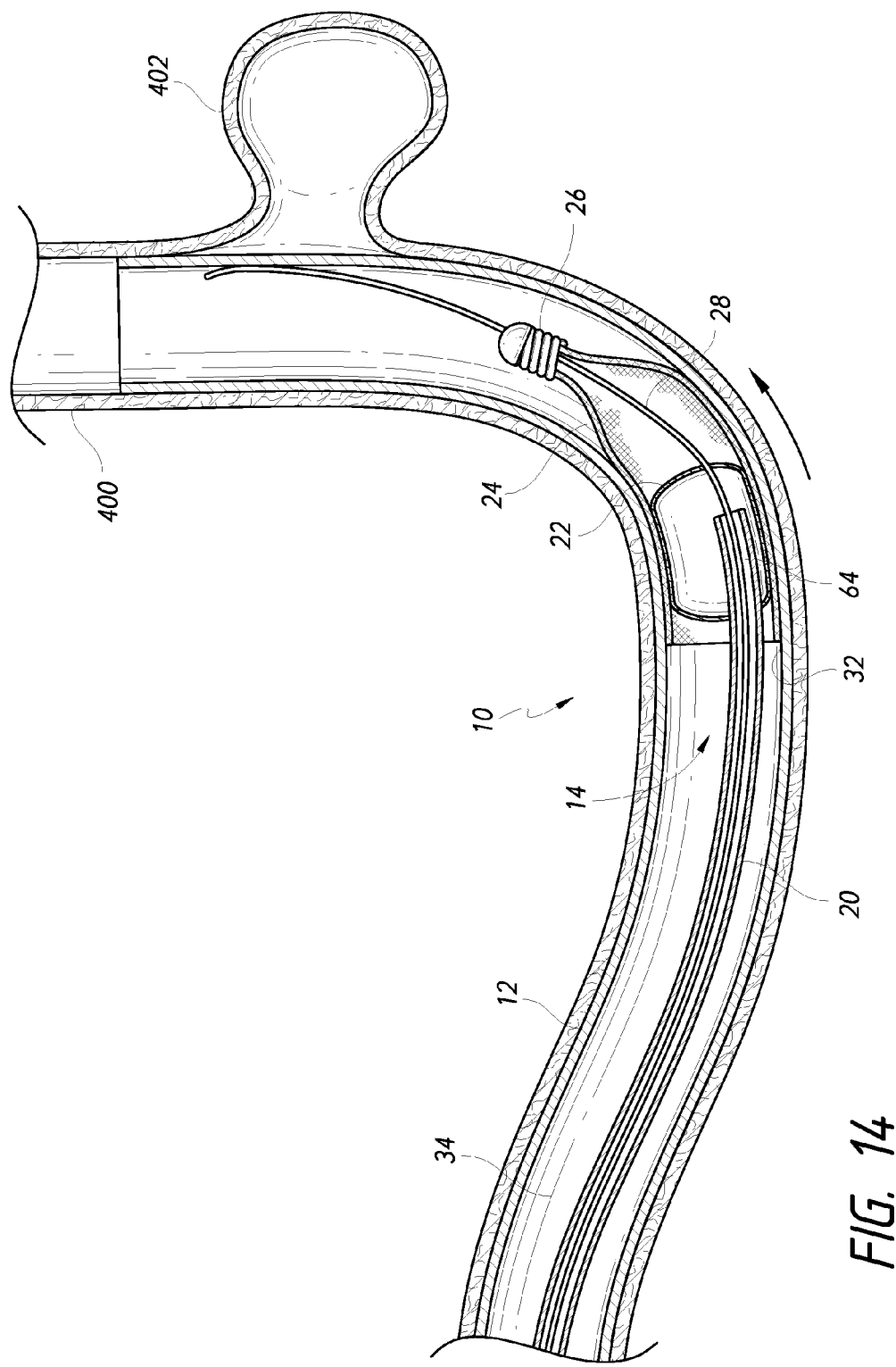
FIGS. 14-16 are cross-sectional side views of a stent delivery system during placement of a stent across an aneurysm, according to some embodiments.
Figure 15:
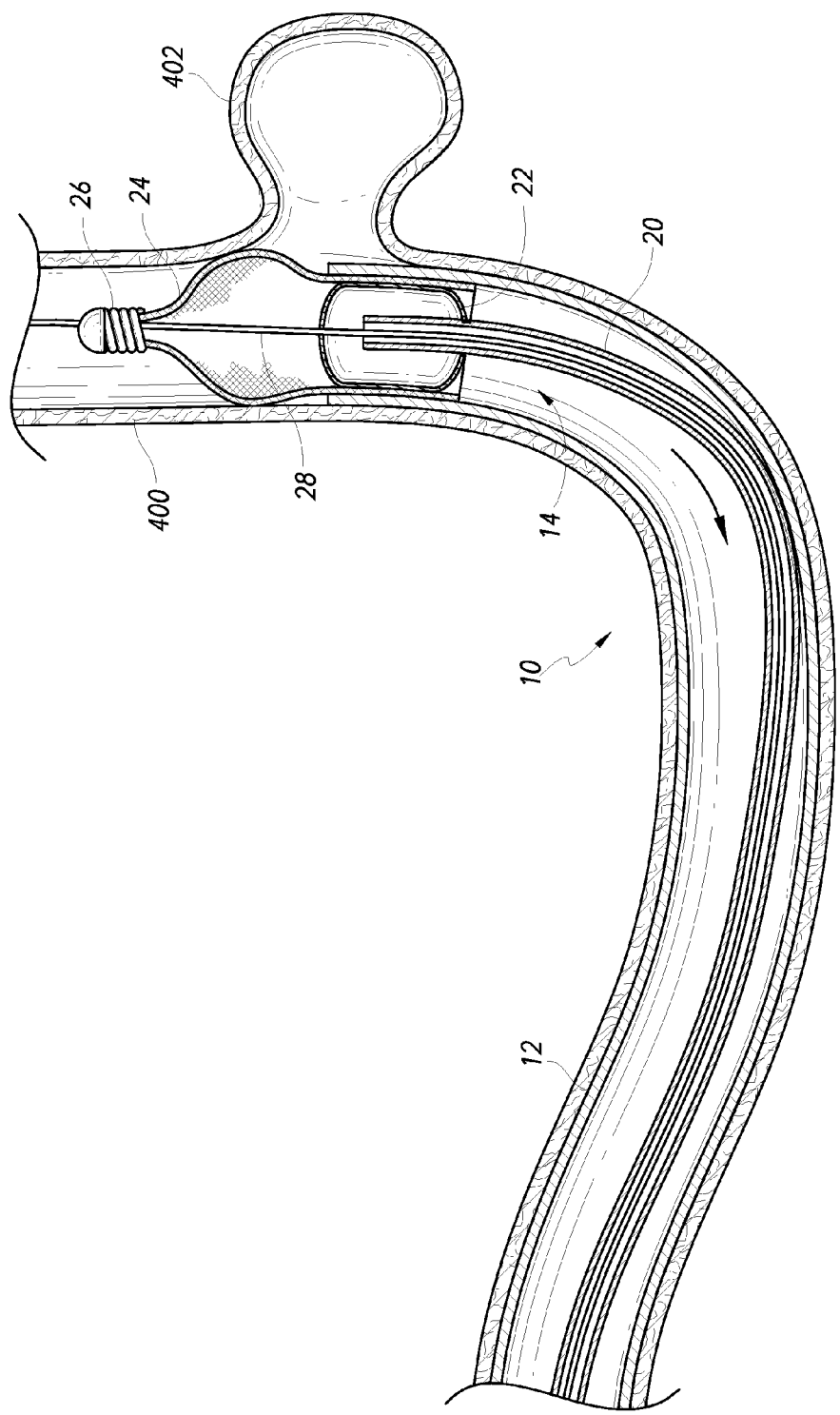
Figure 16:
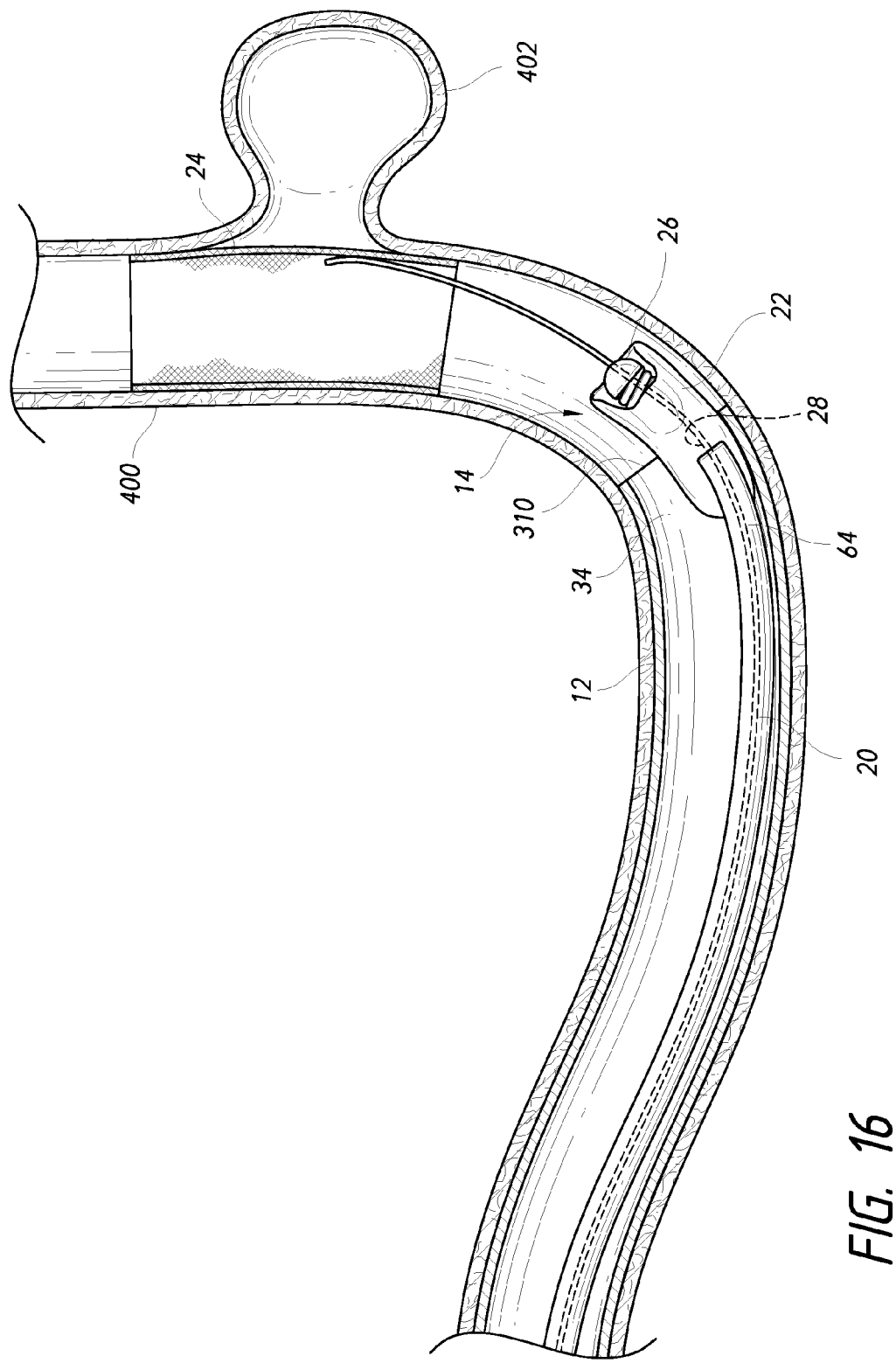

FIGS. 14-16 illustrate a use of the stent delivery system 10 in a vessel 400 having an aneurysm sac 402 and tortuous geometries. As illustrated in FIG. 14, as the core assembly 14 is advanced through the catheter 12 toward the treatment site, the distal and 64 of the core member 20 can tend to be urged against one side or another of the interior surface 32 of the catheter 12. This reflects the reality that during advancement of a core assembly through a catheter lumen, the core assembly will generally not tend to be centered along the longitudinal central axis or middle of the catheter lumen. Instead, a leading end of the core assembly can tend to contact one or another area of the interior surface of the catheter lumen, especially along highly curved sections of the catheter lumen. As this occurs, the distal end of the core member can tend to exert a higher compressive force against the stent, by which it is possible that there be an undue increase the frictional force and/or damage to the structure of the stent. However, some embodiments disclosed herein can mitigate this risk through the use of a highly compliant and resilient engagement member 22.

Therefore, instead of having areas of high force or stress concentration exerted on the stent during advancement of the core assembly 14 through the catheter lumen 34, some embodiments can provide a highly compliant, flexible, and resilient engagement member 22 that can allow these forces and stresses to be distributed along a general section of the engagement member 22, thereby avoiding increased localized forces and stresses. As shown FIG. 14, the distal end 64 of the core member 20 can be permitted to move off-center from the central axis of the catheter lumen 34 at a tortuous segment of the vessel 400, which can cause the engagement member 22 to deflect or deform, thereby allowing stresses and forces to be more evenly distributed about the circumference of the engagement member 22. As in some embodiments discussed herein, the engagement member 22 illustrated in FIG. 14 can comprise one or more balloons attached to the distal end 64 of the core member 20. Generally, an engagement member in the form of a fluid-filled balloon can distort, elongate, compress, expand, or otherwise change shape or size in response to passage through tortuous anatomy, rather than concentrate stress on the stent 24 or other components, as can occur with a solid or rigid engagement member.

After the distal end 64 of the core member 20 is advanced beyond the tortuous section of the vessel 400, the engagement member 22 can tend to recenter the core member distal end 64 along the central axis of the catheter lumen 34, as shown in FIG. 15. FIGS. 15 and 16 illustrate the process of placing and expanding the stent 24 within the vessel 400. As discussed above, the stent 24 can be unsheathed from the catheter 12 and placed into the vessel 400. The engagement member 22 can be used to ensure that the stent 24 is fully expanded into apposition with the vessel wall. Thereafter, the core assembly 14 can be withdrawn into the catheter 12, as illustrated in FIG. 16. In accordance with some embodiments, the engagement member 22 can enclose or enshroud the distal structure 26, thus tending to prevent any snagging or catching of the distal structure 26 when entering the distal end 310 of the catheter 12.

Information regarding additional embodiments of the stent delivery system 100, and additional details and components that can optionally be used or implemented in the embodiments of the stent delivery system described herein, can be found in the above-incorporated U.S. Patent Application Publications Nos. 2011/0152998 A1 and 2009/0318947A1. The stent delivery system 100 disclosed herein can optionally be similar to any of the delivery systems disclosed in these publications, except as further described herein.

The systems and methods discussed herein are not limited to the expansion and use of an stent or occluding device within any particular vessels, but may include any number of different types of vessels. For example, in some aspects, vessels may include arteries or veins. The vessels may have bifurcations and/or sharp turns. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, the delivery system can include an expandable occluding device (e.g., stent) configured to be placed across an aneurysm. The occluding device can be delivered through the distal portion of the catheter, out a distal tip assembly, and into the vasculature adjacent an aneurysm in, for example, the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

The apparatus and methods discussed herein are not limited to the deployment and use of an occluding device or stent within the vascular system but may include any number of further treatment applications. Other treatment sites may include areas or regions of the body such as organ bodies.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

What is claimed is:

1. A stent delivery system, comprising:
   a catheter having an inner wall that defines a lumen;
   a core member extending within the catheter, the core member having a distal segment;
   a self-expanding stent having a length and extending along the core member distal segment radially positioned between the core member and the catheter inner wall;
   an expandable engagement member attached to the core member and extending distally beyond the distal segment of the core member, the engagement member being positioned radially between the core member and the stent and having a length less than 60% of the stent length, the engagement member having (i) an advancement configuration in which the engagement member is expanded within the catheter to press the stent against the catheter inner wall and transmit axial movement of the core member to the stent for moving the stent within the catheter lumen relative to the catheter and (ii) an expansion configuration in which the engagement member extends distally beyond the catheter lumen and expands to a diameter greater than a diameter of the lumen to urge the stent to a fully expanded state;
   wherein the engagement member comprises first and second end portions, the first end portion coupled to the core member, the second end portion positioned distal to and longitudinally spaced apart from a distal end of the core member to permit the second end portion to move freely relative to the core member.

2. The system of claim 1, wherein the engagement member comprises at least one balloon.

3. The system of claim 2, wherein the at least one balloon comprises a material having a durometer of from about Shore 5A to about Shore 60A.

4. The system of claim 3, wherein the at least one balloon comprises a material having a durometer of from about Shore 15A to about Shore 50A.

5. The system of claim 3, wherein the at least one balloon comprises a material having a durometer of from about Shore 20A to about Shore 40A.

6. The system of claim 1, wherein the engagement member length is less than about 40% of the stent length.

7. The system of claim 1, further comprising a distal structure extending distally from the core member distal segment and interposed between an outer surface of the stent and the catheter inner wall.

8. The system of claim 7, wherein the distal structure comprises a coil.

9. The system of claim 1, wherein the engagement member length is less than 40% of the stent length.

10. The system of claim 1, wherein the engagement member length is less than 20% of the stent length.

11. A stent delivery system, comprising:
a catheter having a lumen defined by a catheter inner wall;
a core member extending within the catheter and having a distal segment;
a balloon attached to the distal segment and extending distally beyond the distal segment; and
a self-expanding stent positioned within the catheter and extending over the balloon, the stent having an axial length that is greater than an axial length of the balloon;
wherein the balloon has a length less than 60% of the stent length, the balloon having (i) a collapsed state, (ii) a first expanded state, in which the balloon presses the stent against the catheter inner wall for frictionally engaging the stent with the balloon to move the stent within the catheter lumen as the core member moves relative to the catheter and (iii) a second expanded state, in which the balloon extends distally beyond the catheter lumen and expands to a diameter greater than a diameter of the lumen to urge the stent to a fully expanded state; and
wherein the engagement member comprises first and second end portions, the first end portion coupled to the core member, the second end portion positioned distal to and longitudinally spaced apart from a distal end of the core member to permit the second end portion to move freely relative to the core member.

12. The system of claim 11, wherein the system comprises a plurality of balloons attached to the distal segment.

13. The system of claim 11, wherein the balloon length is less than 40% of the stent length.

14. The system of claim 11, wherein the balloon length is less than 20% of the stent length.

* * * * *